United States Patent
Ahn et al.

(10) Patent No.: US 9,624,334 B2
(45) Date of Patent: Apr. 18, 2017

(54) HYDROPHILICALLY-MODIFIED SILICONE COMPOSITIONS

(75) Inventors: Dongchan Ahn, Midland, MI (US); Qi Huang, La Jolla, CA (US); Maria M. Puscau, Auburn Hills, MI (US); William Schulz, Midland, MI (US); James Thompson, Sanford, MI (US); Kevin Wier, Midland, MI (US)

(73) Assignee: Dow Corning Corporation, Midland, MI (US)

(*) Notice: Subject to any disclaimer, the term of this patent is extended or adjusted under 35 U.S.C. 154(b) by 0 days.

(21) Appl. No.: 13/503,639

(22) PCT Filed: Oct. 19, 2010

(86) PCT No.: PCT/US2010/053145
§ 371 (c)(1),
(2), (4) Date: May 30, 2012

(87) PCT Pub. No.: WO2011/049919
PCT Pub. Date: Apr. 28, 2011

(65) Prior Publication Data
US 2012/0237464 A1    Sep. 20, 2012

Related U.S. Application Data

(60) Provisional application No. 61/254,481, filed on Oct. 23, 2009.

(51) Int. Cl.
| | | |
|---|---|---|
| A61Q 13/00 | (2006.01) | |
| A61Q 15/00 | (2006.01) | |
| A61K 8/81 | (2006.01) | |
| A61K 8/97 | (2006.01) | |
| C08F 290/06 | (2006.01) | |
| A61K 8/89 | (2006.01) | |
| A61Q 19/00 | (2006.01) | |
| C08F 4/52 | (2006.01) | |
| C08F 230/08 | (2006.01) | |

(52) U.S. Cl.
CPC ............ *C08F 290/068* (2013.01); *A61K 8/89* (2013.01); *A61Q 19/00* (2013.01); *C08F 4/52* (2013.01); *C08F 230/08* (2013.01); *A61K 2800/412* (2013.01); *A61K 2800/654* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 4,122,029 A | 10/1978 | Gee et al. | |
| 4,781,917 A | 11/1988 | Luebbe et al. | |
| 4,987,169 A | 1/1991 | Kuwata et al. | |
| 5,387,417 A | 2/1995 | Rentsch | |
| 5,760,116 A | 6/1998 | Kilgour et al. | |
| 5,811,487 A | 9/1998 | Schulz, Jr. et al. | |
| 5,919,441 A | 7/1999 | Mendolia et al. | |
| 5,981,680 A | 11/1999 | Petroff et al. | |
| 6,051,216 A | 4/2000 | Barr et al. | |
| 6,086,903 A | 7/2000 | Trinh et al. | |
| 6,313,249 B1 * | 11/2001 | Nakanishi | C08F 6/02 525/479 |
| 6,346,583 B1 | 2/2002 | Kilgour et al. | |
| 6,444,745 B1 | 9/2002 | Kilgour et al. | |
| 6,531,540 B1 | 3/2003 | O'Brien | |
| 6,538,061 B2 | 3/2003 | Chaiyawat et al. | |
| 6,759,479 B2 | 7/2004 | O'Brien | |
| 6,770,708 B2 | 8/2004 | Kadlec et al. | |
| 7,019,098 B2 | 3/2006 | Hupfield | |
| 7,166,276 B2 | 1/2007 | Stephens et al. | |
| 7,247,622 B2 | 7/2007 | Pfaendler et al. | |
| 7,649,068 B2 | 1/2010 | Ahn | |
| 7,732,543 B2 | 6/2010 | Loch et al. | |
| 7,772,342 B2 | 8/2010 | Tamazawa | |
| 7,850,870 B2 | 12/2010 | Ahn et al. | |
| 8,110,630 B2 | 2/2012 | Lin et al. | |

(Continued)

FOREIGN PATENT DOCUMENTS

| | | |
|---|---|---|
| CN | 101120026 A | 2/2008 |
| CN | 101432341 A | 5/2009 |

(Continued)

OTHER PUBLICATIONS

Dong, Jian; Liu, Zonglin; Han, Nianfeng; Wang, Qin; Xia, Yiran. "Preparation, morphology, and mechanical properties of elastomers based on α ,ω—dihydroxy-polydimethylsiloxane/polystyrene blends", School of Chemistry and Chemical Engineering, Shandong University, Jinan, Peop. Rep. China. Journal of Applied Polymer Science (2004), 92(6), 3542-3548. Publisher: John Wiley & Sons, Inc., CODEN: JAPNAB ISSN: 0021-8995. Journal written in English. CAN 141:107480 AN 2004:416044 CAPLUS (Copyright © 2008 ACS on SciFinder®).

Todd, et al. "Volatile Silicone Fluids for Cosmetics," Cosmetics and Toiletries, 91:29-32 (1976).

Balsam and Sagarin, Cosmetics, Science, and Technology, "Emollient Creams and Lotions," vol. 1, 27-104 , 1972.

Written Opinion of the International Searching Authority Application No. PCT/US2010/053112, dated Jun. 22, 2011, 6 pages.

International Search Report Application No. PCT/US2010/053112, dated Jun. 22, 2011, 3 pages.

Liles, Donald T.; Morita, Yoshitsugu; Kobayashi, Kazuo, Dow Corning Corporation, Midland, MI, USA. "Silicone Elastomeric Powders", *Polymer News*, 2002, vol. 27, pp. 406-411.

(Continued)

*Primary Examiner* — Tigabu Kassa
(74) *Attorney, Agent, or Firm* — Schwegman, Lundberg & Woessner, P.A.

(57) ABSTRACT

In various embodiments, provided are hydrophilically-modified silicone compositions comprising substantially spherical elastomeric microparticles, methods of making such compositions, and silicone pastes, personal care, and healthcare products comprising such silicone compositions.

9 Claims, 5 Drawing Sheets

(56) References Cited

U.S. PATENT DOCUMENTS

| | | |
|---|---|---|
| 8,273,840 B2 | 9/2012 | Lin |
| 8,920,783 B2 | 12/2014 | Lin |
| 2003/0072730 A1 | 4/2003 | Tournilhac |
| 2003/0170188 A1 | 9/2003 | Ferrari et al. |
| 2003/0235553 A1 | 12/2003 | Lu et al. |
| 2004/0180032 A1 | 9/2004 | Manelski et al. |
| 2004/0228821 A1 | 11/2004 | Sunkel et al. |
| 2008/0050552 A1 | 2/2008 | Ahn et al. |
| 2008/0085983 A1 | 4/2008 | Ahn |
| 2010/0183525 A1 | 7/2010 | Lin |
| 2011/0294958 A1 | 12/2011 | Ahn et al. |
| 2012/0219517 A1 | 8/2012 | Ahn et al. |

FOREIGN PATENT DOCUMENTS

| | | |
|---|---|---|
| EP | 1266647 | 12/2002 |
| EP | 1266648 | 12/2002 |
| EP | 1266653 | 12/2002 |
| EP | 2491065 B1 | 11/2014 |
| GB | 2453952 | 4/2009 |
| JP | H07-082327 | 3/1995 |
| JP | 2001-294512 | 10/2001 |
| JP | 2002-255748 | 9/2002 |
| JP | 2006-335978 | 12/2006 |
| JP | 2008-518082 | 5/2008 |
| JP | 2008527077 A | 7/2008 |
| JP | 2009-530476 | 8/2009 |
| JP | 2013-508374 | 3/2013 |
| WO | WO9840425 | 9/1998 |
| WO | WO01/14458 | 3/2001 |
| WO | WO02/28358 | 4/2002 |
| WO | WO03/101412 | 12/2003 |
| WO | WO03/105789 | 12/2003 |
| WO | WO03/105801 | 12/2003 |
| WO | WO03/106614 | 12/2003 |
| WO | WO2004/000247 | 12/2003 |
| WO | WO2004/054523 | 7/2004 |
| WO | WO2004/054524 | 7/2004 |
| WO | WO2004/060101 | 7/2004 |
| WO | WO2004/060271 | 7/2004 |
| WO | WO2004/060276 | 7/2004 |
| WO | WO2006/088571 | 8/2006 |
| WO | WO2007/007403 | 1/2007 |
| WO | WO2007/007521 | 1/2007 |
| WO | WO2007/109282 | 9/2007 |
| WO | WO2008/046762 | 4/2008 |
| WO | WO2009/042732 | 4/2009 |

OTHER PUBLICATIONS

Ginam Kim, Alioscka Sousa, Deborah Meyers, Marilyn Shope, and Matthew Libera, "Diffuse Polymer Interfaces in Lobed Nanoemulsions Preserved in Aqueous Media" Dow Corning Corporation, Science and Technology, Midland, Michigan 48640, and Department of Chemical, Biomedical, and Materials Engineering, Stevens Institute of Technology, Hoboken, New Jersey 07030, 6570 J.AM. CHEM. SOC. 2006, 128, pp. 6570-6571.

Abstract to Darvishi, M. Rezaee; Mirzadeh, H.; Mehrabzadeh, M. Polymer Engineering Department, Amir Kabir University of Technology, Tehran, Iran, "Preparation and study of physical and mechanical properties of biocompatible blends based on poly(dimethylsiloxane) (PDMS) and poly(2-hydroxyethyl methacrylate) (PHEMA)", Iranian Journal of Polymer Science and Technology (Persian Edition) (1998), 11(3), 155-162. Publisher: Iran Polymer Institute, CODEN: IJPTEH ISSN: 1017-6020. Journal written in Persian. CAN 131:59820 AN 1999:269094 CAPLUS.
Newton, Joanna, Stoller, Catherine, and Starch, Michael, "Silicone Technology Offers Novel Methods for Delivering Active Ingredients", Dow Corning Corporation, Midland, Michigan, 5 pages.
Written Opinion of the International Searching Authority Application No. PCT/US2010/053145, dated Dec. 21, 2010, 5 pages.
International Search Report Application No. PCT/US2010/053145, dated Dec. 21, 2010, 3 pages.
Chinese Application Serial No. 201080058663.9, Office Action mailed Feb. 4, 2015, (w/ English Translation), 14 pgs.
Chinese Application Serial No. 201080058663.9, Office Action mailed Feb. 8, 2014, (w/ English Translation), 14 pgs.
Chinese Application Serial No. 201080058663.9, Office Action mailed Jun. 5, 2013, (w/ English Translation), 12 pgs.
Chinese Application Serial No. 201080058663.9, Office Action mailed Aug. 5, 2014, (w/ English Translation), 12 pgs.
Chinese Application Serial No. 201080058663.9, Response filed Apr. 22, 2014 to Office Action mailed Feb. 8, 2014, 13 pgs.
Chinese Application Serial No. 201080058663.9, Response filed Oct. 20, 2014 to Office Action mailed Aug. 5, 2014, 6 pgs.
Chinese Application Serial No. 201080058663.9, Response filed Oct. 21, 2013 to Office Action mailed Jun. 5, 2013, (w/ English Translation of Claims), 19 pgs.
Chinese Application Serial No. 201080058663.9, Voluntary Amendment filed Jan. 25, 2013, (w/ English Translation of Claims), 23 pgs.
European Application Serial No. 10771614.4, Office Action mailed Jan. 14, 2014, 5 pgs.
European Application Serial No. 10771614.4, Office Action mailed May 31, 2012, 2 pgs.
European Application Serial No. 10771614.4, Office Action mailed Jun. 2, 2014, 5 pgs.
European Application Serial No. 10771614.4, Office Action mailed Nov. 13, 2013, 5 pgs.
European Application Serial No. 10771614.4, Response filed May 9, 2014 to Office Action mailed Jan. 14, 2014, 5 pgs.
European Application Serial No. 10771614.4, Response filed Dec. 6, 2012 to Office Action mailed May 31, 2012, 3 pgs.
European Application Serial No. 10771614.4, Response filed Dec. 24, 2013 to Office Action mailed Nov. 13, 2013, 3 pgs.
International Application Serial No. PCT/US2010/053145, International Preliminary Report on Patentability mailed May 3, 2012, 7 pgs.
Japanese Application Serial No. 2012-535293, Amendment filed Jun. 11, 2014, 10 pgs.
Japanese Application Serial No. 2012-535293, Notice of Reasons for Rejection mailed Feb. 18, 2014, (English Translation), 4 pgs.
Japanese Application Serial No. 2012-535293, Notice of Reasons for Rejection mailed Oct. 28, 2014, (w/ English Translation), 4 pgs.
Korean Application Serial No. 10-2012-7013357, Amendment filed May 24, 2012, 12 pgs.

\* cited by examiner

HYDROPHILICALLY-MODIFIED SILICONE COMPOSITIONS

CROSS-REFERENCE TO RELATED APPLICATIONS

This application is a U.S. National Stage of International Application No. PCT/US2010/053145, filed Oct. 19, 2010, which claims the benefit of U.S. Provisional Application No. 61/254,481, filed Oct. 23, 2009, each of which is hereby incorporated by reference herein in its entirety.

In various embodiments, the present application relates to hydrophilically-modified silicone compositions comprising elastomeric microparticles formed by free radical co-polymerization of organopolysiloxanes with organic co-monomers, and methods of making such compositions.

A silicone paste can be generally characterized as having a cross-linked polymeric microparticle matrix (elastomer) component dispersed in a fluid component. The fluid component is sufficiently compatible with the elastomer to become trapped within the matrix and cause swelling of the microparticles. Such silicone compositions have been found to be particularly useful in personal care applications because of their ability to introduce a liquid to skin or hair while imparting a smooth, silky, low-residue feel on dry-down. In addition to fluid, other compounds, such as active ingredients, can be carried within the matrix. Thus, silicone paste compositions are useful for encapsulating a wide variety of active ingredients such as pharmaceutical agents, vitamins, fragrances, oils, and lotions for delivery in cosmetics, personal care and healthcare products.

Attempts to address the ongoing need for silicones with better compatibility, uptake and dispersibility with water, other polar materials and organic compounds, methods of modifying silicones have been developed. For example, WO 2007/007521 A1 teaches coating the surface of a silicone resin with a specific hydrophilic treating agent to render it more dispersible in aqueous dispersion media at pH 3-13. However, this approach does not render the interior of a particle hydrophilic, which makes encapsulation of hydrophilic actives difficult. In another example, WO 2001/014458 teaches a crosslinked hydrosilylation reaction product of an alkenyl-functional silicone compound, a silylhydride functional silicone compound, and one or more allyl-started polyether terminated by a hydrogen, alkyl, aryl, or acyl group. The silicone elastomer was found to exhibit stability and compatibility with polar organic solvents and useful as a component in personal care products. While this approach builds polar functionality into the elastomer, it has intrinsic limitations related to the ease of inhibition of Pt cure catalysts, cost, and discoloration of the Pt catalysts. The water uptake of unsaturated polyethers is also somewhat limited relative to some other organic compounds that are available but unsuitable for hydrosilylation based curing systems.

Recent advances in the preparation of silicone elastomer particles involve the use of free radical polymerization. For example, US 2008/0085983 A1 describes methods of making polymer particles by organoborane-amine complex-catalyzed free radical polymerization or cross-linking of organic or organosilicon monomers, oligomers, and/or polymers in the presence of a poor solvent (a fluid in which the polymerization product is not substantially soluble at the reaction temperature) or a non-solvent (a fluid in which the polymerization product is essentially insoluble at the reaction temperature) for the resulting polymer. However, such methods do not teach pastes comprising hydrophilically-modified microparticles, methods for their preparation, or uses thereof for delivery of personal care or healthcare active ingredients. Thus, there remains a need in the art for such pastes, methods, and applications. There is also need in the art for silicone pastes that have enhanced compatibility with hydrophilic materials but are not subject to the cure inhibition and other limitations of known compositions.

These needs are met by hydrophilically-modified silicone compositions and methods of making such compositions provided by the present invention. According to some embodiments, provided are silicone pastes comprising substantially spherical elastomeric microparticles formed by free radical co-polymerization of organopolysiloxanes with organic co-monomers, wherein the resulting silicone microparticles are insoluble in certain non-solvents. When dispersed in an absorbable fluid to form a paste, such elastomers swell to form substantially spherical swollen microparticles that are useful in a variety of applications, including but not limited to, delivery of active ingredients for personal care and healthcare products.

According to various embodiments, hydrophilically-modified silicone compositions are prepared by a method comprising polymerizing Component (A), at least one organopolysiloxane having an average of at least two free radical polymerizable groups per molecule; and Component (B), at least one organic co-monomer having an average of at least one free radical polymerizable group per molecule; wherein polymerization occurs in the presence of Component (C), at least one organoborane free radical initiator; Component (D), at least one non-solvent that is immiscible with Component (A); optionally, Component (E), at least one organo-nitrogen-reactive compound; and oxygen, while maintaining a temperature of from about 5° C. to about 95° C. to form hydrophilically-modified silicone elastomeric microparticles that are insoluble in Component (D). In various embodiments, the silicone elastomeric microparticles are recovered and dispersed in at least one absorbable fluid to form a paste.

These and additional features and advantages of the invention will become apparent in the course of the following detailed description.

A more complete appreciation of the invention and the many embodiments thereof will be readily obtained as the same becomes better understood by reference to the following detailed description when considered in connection with the accompanying drawings, wherein.

Figure 5:
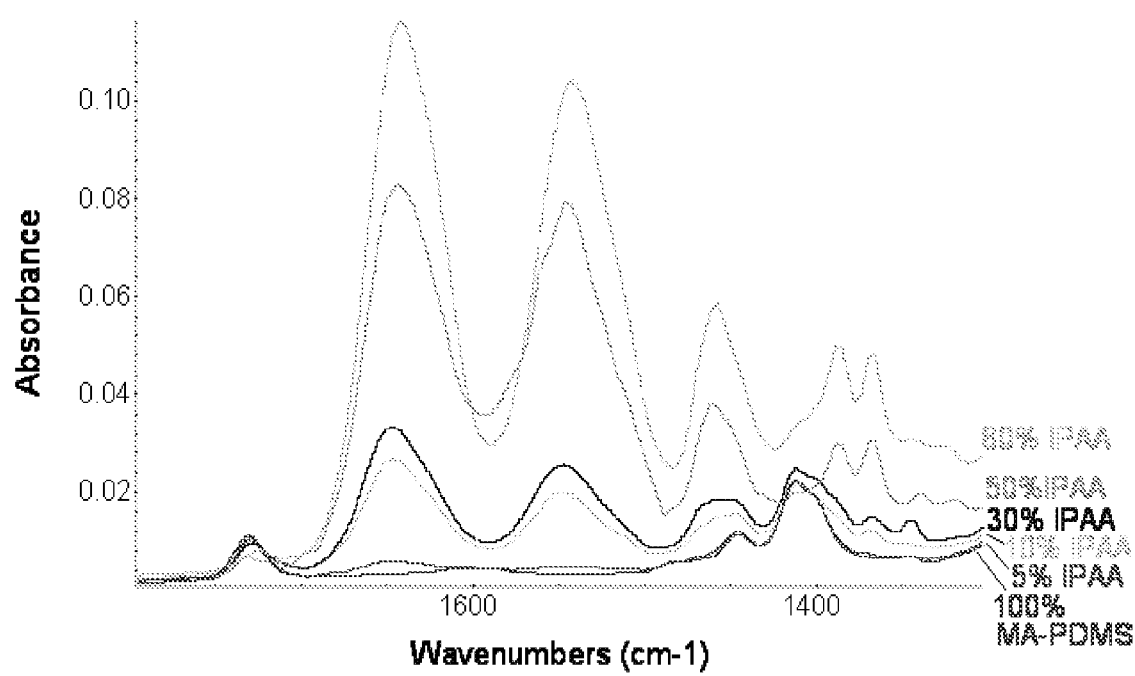
Figure 6:
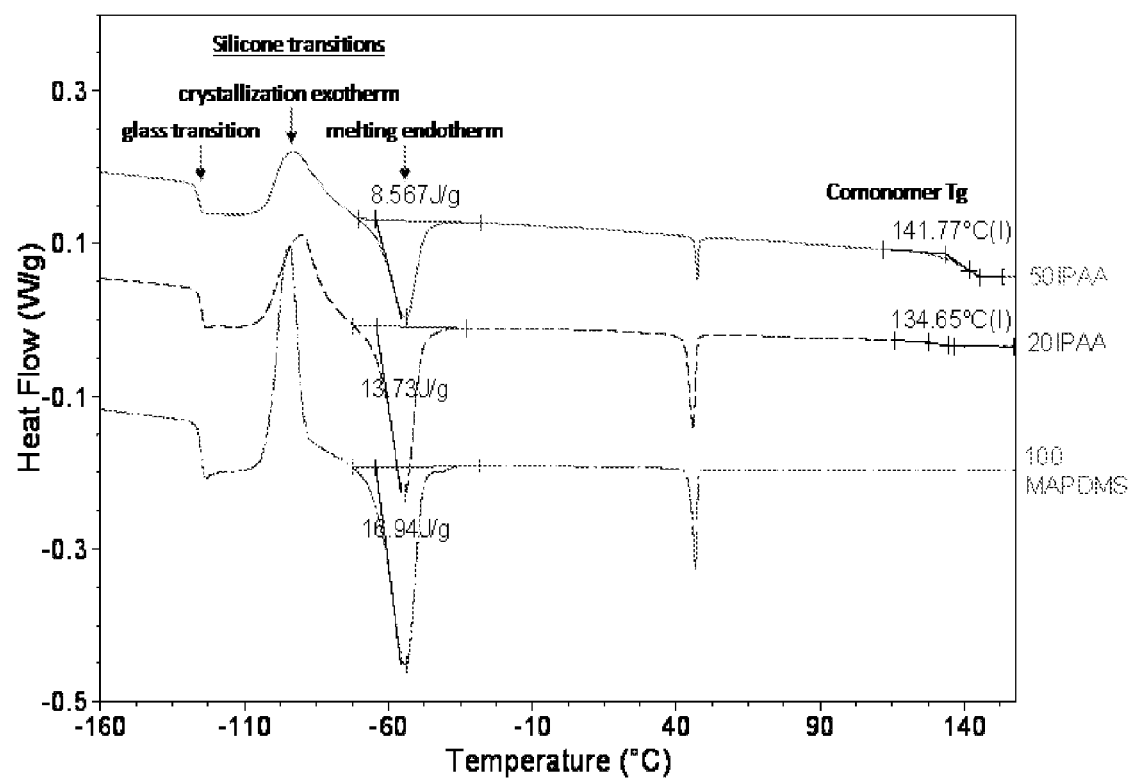

FIG. 5 shows the ATR-IR spectra of polymer particles containing poly(dimethylsiloxane-co-isopropylacrylamide) from Example 23, wherein the initial concentration of IPAA monomer varies from 0-80 wt %, and wherein the amide I (at 1640 cm$^{-1}$) and amide II (1550 cm$^{-1}$) peaks show a corresponding increase of the poly(N-isopropylacrylamide) in the polymer particles FIG. 6 shows the DSC of polymer particles containing poly(dimethylsiloxane-co-isopropylacrylamide) from Examples 20 and 23, wherein the initial concentration of IPAA monomer varies from 0-50 wt %; as the amount of IPAA is increased, the endotherm peak (at 50° C.) area decreases, indicating that poly(n-isopropylacrylamide) has taken the place of some of the siloxane.

Features and advantages of the invention will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

The term "independently selected from," as used in the specification and appended claims, is intended to mean that the referenced groups can be the same, different, or a mixture thereof, unless the context clearly indicates otherwise. Thus, under this definition, the phrase "X$^1$, X$^2$, and X$^3$ are independently selected from noble gases" would include the scenario where X$^1$, X$^2$, and X$^3$ are all the same, where X$^1$, X$^2$, and X$^3$ are all different, and where X$^1$ and X$^2$ are the same but X$^3$ is different.

As used in the specification and appended claims, the term "absorbable fluid" is intended to mean a polar or non-polar fluid that is sufficiently compatible with the resulting elastomer to be absorbed as a diluent. In some embodiments, an absorbable fluid may, but is not required to be, immiscible with water. Examples of fluids suitable for polymer systems can be found in standard polymer handbooks, such as the Polymer Handbook, Third Edition, Edited by J. Brandrup and E. H. Immergut, John Wiley & Sons, Pages VII/379-382+, (1989).

The term "viscosity," as used in the specification and appended claims that pertain to pastes, is intended to mean the value of the real component of the complex viscosity ($\eta'$) measured with a rheometer. Examples of suitable rheometers include, but are not limited to, a Rheometrics RDA II parallel plate rheometer, using a small strain dynamic oscillatory shear experiment at an angular frequency of 10 rad/s; and a Brookfield DV-II+ rheometer with a Helipath attachment and T-D spindle (20.4 mm crossbar) at 2.5 rpm, following the manufacturer's recommended testing procedure and measuring at 25° C. $\eta'$ is a material function that is independent of method as long as comparable testing frequencies and strain rates are used. For simple polymers and fluids, such as the individual components comprising the elastomeric compositions, "viscosity" refers to an extrapolated zero shear viscosity as measured in a small strain dynamic oscillatory shearing experiment at shear rates low enough for $\eta'$ to be relatively independent of shear rate. For pastes, "viscosity" in the examples of this application refer to the measured value of $\eta'$ at the stated frequency and strain rate.

As used in the specification and appended claims, the term "substantially spherical" is intended to mean absolutely spherical as well as primarily spherical. Thus, the phrase "substantially spherical particles" is intended to encompass individual (or primary) particles that would have essentially spherical morphology but for minor deviations. The phrase is also intended to encompass a sample having more spherical particles than non-spherical particles.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

Among other things, provided herein are silicone compositions comprising substantially spherical hydrophilic elastomeric microparticles formed by free radical co-polymerization of organopolysiloxanes with organic co-monomers, methods of preparing such compositions, and personal care and healthcare products comprising such compositions. In some embodiments, hydrophilically-modified silicone elastomers are formed by an emulsion polymerization process.

Emulsion polymerization of monomers by free radical techniques is known in the art. For example, Kim et al. in *J. Am. Chem. Soc.* 2006, 128, 6570-6571, have shown by transmission electron microscopy (TEM) and electron energy loss spectroscopy (EELS) that methyl acrylate, methyl methacrylate or vinyl acetate monomers polymerized in seed latex particles of polydimethylsiloxane suspended in water form acorn-shaped biphasic particles with two hemispherical lobes that result from phase separation of the polymerized acrylate and polydimethylsiloxane constituents with a relatively broad interface. This is suggestive of some copolymer compatibilization, wherein one of the lobes is essentially silicone-free, thereby rendering the particles non-continuous in silicone. However, there is no known indication in the art that a substantially spherical, globally homogeneous elastomeric microparticle with a uniform, continuous silicone phase could be formed by a free radical copolymerization process in emulsion. Further, there is no known indication in the art that pastes obtained by combining products of emulsion-based free radical copolymerization of a silicone and acrylic monomers with silicone-compatible solvents would exhibit physical properties similar to hydrosilylation cured silicone based pastes while also permitting enhanced uptake of polar substances.

In various embodiments, provided are methods for the preparation of hydrophilically-modified silicone compositions. Such methods comprise polymerizing Component (A), at least one organopolysiloxane having an average of at least two free radical polymerizable groups per molecule; and Component (B), at least one organic co-monomer having an average of at least one free radical polymerizable group per molecule; wherein polymerization occurs in the presence of Component (C), at least one organoborane free radical initiator; Component (D), at least one non-solvent that is immiscible with Component (A); optionally, Component (E), at least one organonitrogen-reactive compound; optionally, Component (F), at least one active ingredient suitable for use in personal care and healthcare products; optionally, Component (G), at least one emulsifier; and oxygen, while maintaining a temperature of from about 5° C. to about 95° C. to form hydrophilically-modified silicone elastomeric microparticles. In some embodiments, the insoluble silicone elastomeric microparticles formed may be recovered and dispersed in at least one absorbable fluid to form a paste. In some embodiments, the absorbable fluid is absorbed by the microparticles to form substantially spherical swollen silicone particles.

In some embodiments, silicone elastomeric microparticles are formed by adding Component (C) to a dispersion or emulsion comprising Component (A), Component (B), Component (D), and Component (E). In some embodiments, silicone elastomeric microparticles are formed by adding Component (E) to a dispersion or emulsion comprising Component (A), Component (B), Component (C) and Component (D). According to various embodiments, provided are pastes comprising hydrophilically-modified silicone elastomeric microparticles prepared by a process comprising (I) polymerizing Component (A), and Component (B) in the presence of Component (C); Component (D); optionally, Component (E); optionally, Component (F); optionally, Component (G); and oxygen, while maintaining a temperature of from about 5° C. to about 95° C. to form hydrophilically-modified silicone elastomeric microparticles that are insoluble in Component (D); and (II) recovering the silicone elastomeric microparticles and dispersing them in at least one absorbable fluid.

Component (A), Free Radical Polymerizable Organopolysiloxane

Generally, Component (A) comprises organopolysiloxanes having free radical polymerizable moieties; siloxane resins; or a combination thereof. Said organopolysiloxanes can be polymeric or a mixture of oligomers and polymers, and polymeric organopolysiloxanes can either be homopolymeric or heteropolymeric. In addition, the organopolysiloxanes can be linear, branched, or hyperbranched in structure. Component (A) undergoes free radical-catalyzed addition polymerization, and in some embodiments, can also undergo co-polymerization and/or cross-linking.

In some embodiments, Component (A) comprises organopolysiloxanes having at least two free radical polymerizable moieties per molecule, wherein such moieties are monofunctional, multifunctional, or a combination thereof. Thus, Component (A) can be a mixture of organopolysiloxanes differing in their degree of functionality and/or the nature of the free radical polymerizable moieties. The organopolysiloxanes of Component (A) can also vary in consistency from a fluid to a gum. For example, the organopolysiloxane can be a fluid, a solid, or a solid that becomes flowable at an elevated temperature or by the application of shear. In some embodiments, the organopolysiloxanes have a viscosity of from about 1 cP to about 5,000,000 cP at 25° C.; alternatively, from about 50 cP to about 500,000 cP at 25° C.; alternatively, from about 100 cP to about 100,000 cP at 25° C.

The organopolysiloxanes of Component (A) may also have a glass transition temperature or, upon polymerization or crosslinking, form particles that have a glass transition temperature, wherein the resulting silicone composition undergoes marked changes in its viscosity under the temperatures of use. Such compositions are particularly useful for encapsulation of active ingredients that are released by the introduction of heat.

In some embodiments, Component (A) may comprise free radical polymerizable organopolysiloxanes having formulae selected from:

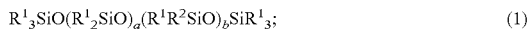 (1)

wherein a has a value of zero to 20,000 and b has a value of 1 to 20,000; and wherein each $R^1$ group is independently a hydrogen, halogen, or a monovalent organic group, and each $R^2$ group is independently a monovalent unsaturated organic group; and

 (2)

wherein c has a value of zero to 20,000, and d has a value of zero to 20,000; and wherein each $R^3$ is independently a hydrogen, halogen, or a monovalent organic group, and each $R^4$ group is independently a monovalent unsaturated organic group.

Suitable $R^1$ and $R^3$ groups include, but are not limited to, hydrogen; organic groups (linear and/or branched) such as alkyl groups, haloalkyl groups, alkenyl groups, alkynyl groups, acrylate functional groups, and methacrylate functional groups; and other organic functional groups such as glycidyl groups, amine groups, ether groups, cyanate ester groups, isocyano groups, ester groups, carboxylic acid groups, carboxylate salt groups, succinate groups, anhydride groups, mercapto groups, sulfide groups, azide groups, phosphonate groups, phosphine groups, masked isocyano groups, and hydroxyl groups. Examples of such groups include, but are not limited to, acrylic functional groups such as acryloyloxypropyl groups and methacryloyloxypropyl groups; alkyl groups such as methyl, ethyl, propyl, isopropyl, n-butyl, s-butyl, and t-butyl groups; alkenyl groups such as vinyl, allyl, and butenyl groups; alkynyl groups such as ethynyl and propynyl groups; aromatic groups such as phenyl, tolyl, and xylyl groups; cyanoalkyl groups such as cyanoethyl and cyanopropyl groups; halogenated hydrocarbon groups such as 3,3,3-trifluoropropyl, 3-chloropropyl, dichlorophenyl, and 6,6,6,5,5,4,4,3,3-nonafluorohexyl groups; alkenyloxypoly(oxyalkyene) groups such as allyloxy(polyoxyethylene), allyloxypoly(oxypropylene), and allyloxy-poly(oxypropylene)-co-poly(oxyethylene) groups; alkyloxypoly(oxyalkyene) groups such as propyloxy(polyoxyethylene), propyloxypoly(oxypropylene), and propyloxy-poly(oxypropylene)-co-poly(oxyethylene) groups; halogen substituted alkyloxypoly(oxyalkyene) groups such as perfluoropropyloxy(polyoxyethylene), perfluoropropyloxypoly(oxypropylene), and perfluoropropyloxy-poly(oxypropylene)-co-poly(oxyethylene) groups; alkoxy groups such as methoxy, ethoxy, n-propoxy, isopropoxy, n-butoxy, and ethylhexyloxy groups; aminoalkyl groups such as 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole groups; epoxyalkyl groups such as 3-glycidoxypropyl, 2-(3,4,-epoxycyclohexyl)ethyl, and 5,6-epoxyhexyl groups; ester functional groups such as actetoxyethyl and benzoyloxypropyl groups; hydroxy functional groups such as hydroxy and 2-hydroxyethyl groups; isocyanate and masked isocyanate functional groups such as 3-isocyanatopropyl, tris-3-propylisocyanurate, propyl-t-butylcarbamate, and propylethylcarbamate groups; aldehyde functional groups such as undecanal and butyraldehyde groups; anhydride functional groups such as 3-propyl succinic anhydride and 3-propyl maleic anhydride groups; carboxylic acid functional groups such as 3-carboxypropyl and 2-carboxyethyl groups; and metal salts of carboxylic acids such as the zinc, sodium, or potassium salts of 3-carboxypropyl and 2-carboxyethyl.

Suitable $R^2$ and $R^4$ groups include, but are not limited to, monovalent alkenyl and alkynyl groups having 2-12 carbon atoms groups such as vinyl, allyl, butenyl, ethynyl, and propynyl groups; alkenyloxypoly(oxyalkyene) groups such as allyloxy(polyoxyethylene), allyloxypoly(oxypropylene), and allyloxy-poly(oxypropylene)-co-poly(oxyethylene) groups; acrylic functional groups such as acryloyloxypropyl and methacryloyloxypropyl groups; and halogen-substituted analogs thereof. In certain embodiments, $R^2$ and $R^4$ are selected from acrylate groups and methacrylate groups.

Some representative examples of Component (A) include, but are not limited to, methacryloxypropyldimethylsiloxy-terminated polydimethylsiloxane; acryloxypropyldimethyl-siloxy-terminated polydimethylsiloxane, 1,3-bis(methacryloxypropyl)tetramethyldisiloxane, 1,3-bis(acryloxypropyl) tetramethyldisiloxane, 1,3-bis(methacryloxymethyl) tetramethyldisiloxane, 1,3-bis(acryloxymethyl) tetramethyldisiloxane, α,ω-methacryloxymethyldimethylsilyl terminated polydimethylsiloxane, methacryloxypropyl-terminated polydimethylsiloxane, α,ω-acryloxymethyldimethylsilyl terminated polydimethylsiloxane, methacryloxypropyldimethylsilyl terminated polydimethylsiloxane, α,ω-acryloxypropyldimethylsilyl terminated polydimethylsiloxane, pendant acrylate and methacrylate functional polymers such as poly(acryloxypropyl-methylsiloxy) polydimethylsiloxane and poly(methacryloxypropyl-methylsiloxy) polydimethylsiloxane copolymers, telechelic polydimethylsiloxanes having multiple acrylate or methacrylate functional groups including those formed via a Michael addition reaction of multi-acrylate or multi-methacrylate monomers to amine-terminated polydimethylsiloxanes, and combinations thereof. Also suitable for use as free radical polymerizable organosilicon compounds include monofunctional acrylate or methacrylate terminated organopolysiloxanes such as polydimethylsiloxane terminated at one end by a methacryloxypropyldimethylsilyl group and terminated at the other end by n-butyldimethylsilyl groups.

In some embodiments, Component (A) may comprise siloxane resins having structural units of organopolysiloxanes independently selected from:

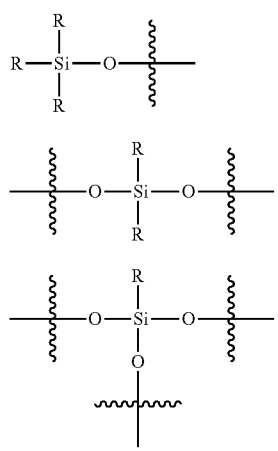

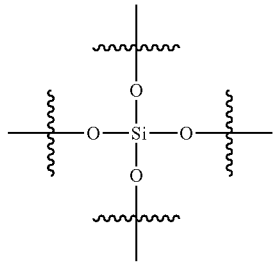

wherein M represents a monofunctional unit $R_3SiO_{1/2}$; D represents a difunctional unit $R_2SiO_{2/2}$; T represents a trifunctional unit $RSiO_{3/2}$; and Q represents a tetrafunctional unit $SiO_{4/2}$.

In some embodiments, Component (A) may comprise a siloxane resin selected from MQ resins having $R^5{}_3SiO_{1/2}$ units and $SiO_{4/2}$ units; TD resins having $R^5SiO_{3/2}$ units and $R^5{}_2SiO_{2/2}$ units; MT resins having $R^5{}_3SiO_{1/2}$ units and $R^5SiO_{3/2}$ units; MTD resins having $R^5{}_3SiO_{1/2}$ units, $R^5SiO_{3/2}$ units, and $R^5{}_2SiO_{2/2}$ units, and combinations thereof; wherein each $R^5$ group is independently a monovalent organic group having from 1-20 carbon atoms. In some embodiments, $R^5$ has from 1-10 carbon atoms. In some embodiments, at least one $R^5$ group is a free radical polymerizable unsaturated organic group.

Suitable examples of $R^5$ include, but are not limited to, acrylate functional groups such as acryloxyalkyl groups; methacrylate functional groups such as methacryloxyalkyl groups; cyanofunctional groups; monovalent hydrocarbon groups; and combinations thereof. The monovalent hydrocarbon groups may include alkyl groups such as methyl, ethyl, propyl, isopropyl, n-butyl, s-butyl, t-butyl, pentyl, neopentyl, octyl, undecyl, and octadecyl groups; cycloalkyl groups such as cyclohexyl groups; alkenyl groups such as vinyl, allyl, butenyl, and hexenyl groups; alkynyl groups such as ethynyl, propynyl, and butynyl groups; aryl groups such as phenyl, tolyl, xylyl, benzyl, and 2-phenylethyl groups; halogenated hydrocarbon groups such as 3,3,3-trifluoropropyl, 3-chloropropyl, dichlorophenyl, and 6,6,6, 5,5,4,4,3,3-nonafluorohexyl groups; and combinations thereof. The cyano-functional groups may include cyanoalkyl groups such as cyanoethyl and cyanopropyl groups, and combinations thereof.

$R^5$ may also include alkyloxypoly(oxyalkyene) groups such as propyloxy(polyoxyethylene), propyloxypoly(oxypropylene) and propyloxy-poly(oxypropylene)-co-poly (oxyethylene) groups, halogen substituted alkyloxypoly (oxyalkyene) groups such as perfluoropropyloxy (polyoxyethylene), perfluoropropyloxypoly(oxypropylene) and perfluoropropyloxy-poly(oxypropylene) copoly(oxyethylene) groups, alkenyloxypoly(oxyalkyene) groups such as allyloxypoly(oxyethylene), allyloxypoly(oxypropylene) and allyloxy-poly(oxypropylene) copoly(oxyethylene) groups, alkoxy groups such as methoxy, ethoxy, n-propoxy, isopropoxy, n-butoxy and ethylhexyloxy groups, aminoalkyl groups such as 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole groups, hindered aminoalkyl groups such as tetramethylpiperidinyl oxypropyl groups, epoxyalkyl groups such as 3-glycidoxypropyl, 2-(3, 4,-epoxycyclohexyl)ethyl, and 5,6-epoxyhexyl groups, ester functional groups such as acetoxymethyl and benzoyloxypropyl groups, hydroxyl functional groups such as hydroxy and 2-hydroxyethyl groups, isocyanate and masked isocyanate functional groups such as 3-isocyanatopropyl, tris-3-propylisocyanurate, propyl-t-butylcarbamate, and propylethylcarbamate groups, aldehyde functional groups such as undecanal and butyraldehyde groups, anhydride functional groups such as 3-propyl succinic anhydride and 3-propyl maleic anhydride groups, carboxylic acid functional groups such as 3-carboxypropyl, 2-carboxyethyl, and 10-carboxydecyl groups, metal salts of carboxylic acids such as zinc, sodium, and potassium salts of 3-carboxypropyl and 2-carboxyethyl groups, and combinations thereof.

Some specific examples of suitable siloxane resins that can be used as Component (A) include, but are not limited to, $M^{Methacryloxymethyl}Q$ resins; $M^{Methacryloxypropyl}Q$ resins; $MT^{Methacryloxymethyl}T$ resins; $MT^{Methacryloxypropyl}T$ resins; $MDT^{Methacryloxymethyl}T^{Phenyl}T$ resins; $MDT^{Methacryloxypropyl}T^{Phenyl}T$ resins; $M^{Vinyl}T^{Phenyl}$ resins; $TT^{Methacryloxymethyl}$ resins; $TT^{Methacryloxypropyl}$ resins; $T^{Phenyl}T^{Methacryloxymethyl}$ resins; $T^{Phenyl}T^{Methacryloxypropyl}$ resins; $TT^{Phenyl}T^{Methacryloxymethyl}$ resins; $TT^{Phenyl}T^{Methacryloxypropyl}$ resins; and combinations thereof.

Siloxane resins may be prepared by any method known in the art. In some embodiments, the resin is made by treating a resin copolymer produced by a silica hydrosol capping process with an alkenyl including endblocking reagent. This preferably includes reacting a silica hydrosol under acidic conditions with a hydrolyzable triorganosilane such as trimethylchlorosilane, a siloxane such as hexamethyldisiloxane, and combinations thereof, and then recovering a copolymer having M and Q groups including 2 to 5% wt of hydroxyl groups. The copolymer may be reacted with an endblocking agent including unsaturated organic groups and an endblocking agent free of aliphatic unsaturation in amounts sufficient to provide 3 to 30 mole percent of unsaturated organofunctional M, D or T groups in the resin relative to the sum of all M, D, T and Q units comprising the resin. Suitable endblocking agents include silazanes, siloxanes, silanes, and combinations thereof.

In some embodiments, Component (A) is selected from acrylate and methacrylate-functional polydimethylsiloxanes and resins. Good results have been achieved with the selection of methacrylate-terminated polydimethylsiloxanes and acrylate-terminated polydimethylsiloxanes.

Component (B), Polymerizable Co-Monomer

Generally, Component (B) comprises at least one organic co-monomer capable of free radical polymerization. In some embodiments, Component (B) is an organic co-monomer having at least one free radical polymerizable group per molecule. In some embodiments, the organic co-monomer of Component (B) has at least one hydrophilic group per molecule. Examples of suitable organic compounds include, but are not limited to, 2-ethylhexylacrylate, 2-ethylhexylmethacrylate, methylacrylate, methylmethacrylate, neopentyl glycol diacrylate, neopentyl glycol dimethacrylate, glycidyl acrylate, glycidyl methacrylate, allyl acrylate, allyl methacrylate, strearyl acrylate, tetrahydrofuryl methacrylate, caprolactone acrylate, perfluorobutyl acrylate, perfluorobutyl methacrylate, 1H, 1H, 2H, 2H-heptadecafluorodecyl acrylate, 1H, 1H, 2H, 2H-heptadecafluorodecyl methacrylate, tetrahydroperfluoro acrylate, phenoxyethyl acrylate, phenoxyethyl methacrylate, bisphenol A acrylate, bisphenol A dimethacrylate, ethoxylated bisphenol A acrylate, ethoxylated bisphenol A methacrylate, hexafluoro bisphenol A diacrylate, hexafluoro bisphenol A dimethacrylate, diethylene glycol diacrylate, diethylene glycol dimethacrylate, dipropylene glycol diacrylate, dipropylene glycol dimethacrylate, polyethylene glycol diacrylate, polyethylene glycol dimethacrylate, polypropylene glycol methacrylate, polypropylene glycol diacrylate, polypropylene glycol dimethacrylate, propylene glycol monomethacrylate, ethylene glycol mono-methacrylate, N-isopropyl acrylamide, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, methyl-3-butenoate, allyl methyl carbonate, diallyl pyrocarbonate, allyl acetoacetate, diallyl carbonate, diallyl phthalate, dimethyl itaconate, diallyl carbonate, or combinations thereof. Other useful organic compounds include (meth)acrylate tipped polyurethane prepolymers prepared by reacting isocyanate reactive acrylate monomers, oligomers or polymers such as hydroxy acrylates with isocyanate functional prepolymers, (meth)acrylate tipped rubbery oligomers and polymers such as acrylate- or methacrylate-tipped polyisobutylenes, and (meth)acrylate functionalized natural oil derivatives such as methacrylate-functionalized soybean oil. One of skill in the art will recognize that the selection of the organic compound for Component (B) will depend upon, among other things, the nature of Component (A) and the desired use of the resulting product.

In some embodiments, Component (B) may be an organic acid (for example, acrylic acid). When Component (B) is an organic acid, the acid may also serve as an organonitrogen-reactive compound.

While numerous organic co-monomers are suitable as Component (B), good results have been obtained with the selection of methyl methacrylate, stearyl methacrylate, n-butyl acrylate, 2-hydroxyethyl methacrylate, benzyl methacrylate, tetrahydrofuryl methacrylate, dimethylaminoethyl methacrylate, N,N-dimethylacrylamide, n-vinyl formamide, 4-vinyl pyridine, 1-vinyl-2-pyrolidone, and N-isopropylacrylamide as Component (B).

In some embodiments, Component (B) is from about 0.1% to about 50% (by weight) of the silicone composition; alternatively, from about 1% to about 40% (by weight) of the silicone composition; alternatively, from about 2.5% to about 25% (by weight) of the silicone composition.

Component (C), Organoborane Free Radical Initiator

Generally, Component (C) comprises at least one organoborane compound that is capable of generating a free radical and initiating free radical addition polymerization and/or crosslinking. Stabilized organoborane compounds that render the organoborane non-pyrophoric at ambient conditions may be used. In some embodiments, Component (C) is a complex formed between an organoborane and a suitable organonitrogen (for example, an amine) that renders the complex stable at ambient conditions, wherein a free radical is generated (and polymerization is initialized) upon introduction of an organonitrogen-reactive compound in the presence of oxygen. In some embodiments, Component (C) is an organoborane compound wherein a free radical is generated (and polymerization is initiated) upon heating. In some embodiments, Component (C) is a solvent-stabilized organoborane (for example, a solution of a trialkylborane in THF) where the solvent is allowed to evaporate to liberate the borane and thereby create a radical.

In some embodiments, Component (C) is an organoborane-organonitrogen complex that may be selected from complexes having the formula:

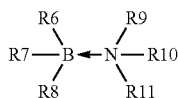

wherein B represents boron and N represents nitrogen; wherein at least one of R6, R7, and R8 contains one or more silicon atoms with the silicon-containing group(s) covalently attached to boron; wherein R6, R7, and R8 are groups that can be independently selected from hydrogen, a cycloalkyl group, a linear or branched alkyl group having 1-12 carbon atoms on the backbone, an alkylaryl group, an organosilane group such as an alkylsilane or an arylsilane group, an organosiloxane group, an alkylene group capable of functioning as a covalent bridge to another boron atom, a divalent organosiloxane group capable of function as a covalent bridge to another boron atom, or halogen substituted homologues thereof; wherein R9, R10, and R11 are groups that yield an amine compound or a polyamine compound capable of complexing with boron and are independently selected from hydrogen, an alkyl group containing 1-10 carbon atoms, a halogen substituted alkyl group containing 1-10 carbon atoms, or an organosilicon functional group; and wherein at least two of the R6, R7, and R8 groups and at least two of the R9, R10, and R11 groups can combine to form heterocyclic structures, provided that the sum of the number of atoms from the two combining groups does not exceed 11.

In some embodiments, Component (C) may be selected from alkylborane-organonitrogen complexes that include, but are not limited to, trialkylborane-organonitrogen complexes comprising trialkylboranes having the formula $BR''_3$, wherein R" represents linear and branched aliphatic or aromatic hydrocarbon groups containing 1-20 carbon atoms. Examples of suitable trialkylboranes include, but are not limited to, trimethylborane, tri-n-butylborane, tri-n-octylborane, tri-sec-butylborane, tridodecylborane, and phenyldiethylborane.

Examples of suitable organonitrogens for forming the organoborane-organonitrogen complexes of Component (C) include, but are not limited to, 1,3 propane diamine; 1,6-hexanediamine; methoxypropylamine; pyridine; isophorone diamine; and silicon-containing amines such as 3-aminopropyltrimethoxysilane, 3-aminopropyltriethoxysilane, 2-(trimethoxysilylethyl)pyridine, aminopropylsilanetriol, 3-(m-aminophenoxy)propyltrimethoxysilane, 3-aminopropyldiisopropylmethoxysilane, aminophenyltrimethoxysilane, 3-aminopropyltris(methoxyethoxethoxy)silane, N-(2-aminoethyl)-3-aminopropyltrimethoxysilane, N-(6-aminohexyl)aminomethyltrimethoxysilane, N-(2-aminoethyl)-hI-aminoundecyltrimethoxysilane, (aminoethylaminomethyl)benethyltrimethoxysilane, N-(2-aminoethyl)-3-aminopropylmethyldimethoxysilane, N-(2-aminoethyl)-3-aminoisobutylmethyldimethoxysilane, and (3-trimethoxysilylpropyl)diethylene-triamine.

In some embodiments, nitrogen-containing compounds that may be useful for forming the organoborane-organonitrogen complexes of Component (C) may be selected from organopolysiloxanes having least one amine functional group. Examples of suitable amine functional groups include, but are not limited to, 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole. Such organopolysiloxanes include, but are not limited to, those having formulas similar to the previously described formulas (1) and (2). Other nitrogen-containing compounds that may be useful for forming the organoborane-organonitrogen complexes of Component (C) include, but are not limited to, N-(3-triethyoxysilylpropyl)-4,5-dihydroimidazole, ureidopropyltriethoxysilane, siloxanes having formulas similar to the previously described formulas (1) and (2), and organopolysiloxane resins in which at least one group is an imidazole, amidine, or ureido functional group.

In some embodiments, a free radical is generated by, and polymerization and/or crosslinking is initiated by, heating an organoborane compound (preferably organoborane-organonitrogen complex) or by simply exposing an anaerobically contained alkylborane of Component (C) to air. In some embodiments, a free radical is generated by, and polymerization and/or crosslinking is initiated by, heating an organoborane-organonitrogen complex of Component (C), wherein heating causes dissociation of the complex. In some embodiments, a free radical is generated by, and polymerization and/or crosslinking is initiated by, combining an organonitrogen-reactive compound of Component (E) [or in some embodiments, an organonitrogen-reactive Component (B)] with an organoborane-organonitrogen complex of Component (C) in an oxygen environment, wherein the combination causes dissociation of the complex. With respect to the latter, a free radical can be generated at temperatures below the dissociation temperature of the organoborane-organonitrogen complex, such as at or below ambient temperature.

Although organonitrogen-stabilized organoborane compounds are particularly useful as Component (C), one of skill in the art will understand that any organoborane may be used. Examples of alternate stabilized forms of organoboranes useful for this invention, include ring stabilized compounds, such as 9-BBN, or solvent complexed organoboranes such as trialkylborane-THF solutions.

In some embodiments, Component (C) is a trialkylborane-organonitrogen complex wherein the trialkylborane is selected from triethylborane, tri-n-butylborane, tri-n-octylborane, tri-sec-butylborane, and tridodecylborane. Good results have been obtained with the selection of triethylborane-propanediamine (TEB-PDA), triethylborane-butylimidazole (TEB-BI), and triethylborane-methoxypropylamine (TEB-MOPA) complexes, and tri-n-butylborane methoxypropyl amine.

Component (D), Non-Solvents

Generally, Component (D) comprises at least one non-solvent that is immiscible with Component (A). In some embodiments, Component (D) is sufficiently incompatible with the silicone elastomers formed by polymerization of the other components to result in little or no swelling of the elastomers by Component D. In some embodiments, Component (D) is selected from water, acetone, and lower alcohols such as methanol, or combinations thereof.

Optional Component (E), Organonitrogen-Reactive Compound

Generally, optional Component (E) comprises at least one organonitrogen-reactive compound that, when combined with the organoborane-organonitrogen complex of Component (C) and exposed to an oxygenated environment, is capable of causing the organoborane-organonitrogen complex to dissociate, thereby initiating free radical polymerization and/or crosslinking. The presence of such an organonitrogen-reactive compound allows for polymerization and/or crosslinking to occur rapidly at temperatures below the dissociation temperature of the organoborane-organonitrogen complexes of Component (C), including at room temperature and below.

Some examples of suitable organonitrogen-reactive compounds of Component (E) include, but are not limited to, mineral acids, Lewis acids, carboxylic acids, carboxylic acid derivatives such as anhydrides and succinates, carboxylic acid metal salts, isocyanates, aldehydes, epoxides, acid chlorides, and sulphonyl chlorides, acetic acid, acrylic acid, methacrylic acid, polyacrylic acid, polymethacrylic acid, methacrylic anhydride, undecylenic acid, oleic acid, stearic acid, citric acid, levulinic acid, 2-carboxyethyl acrylate, isophorone diisocyanate monomers or oligomers, methacryloylisocyanate, 2-(methacryloyloxy)ethyl acetoacetate, undecylenic aldehyde, and dodecyl succinic anhydride. In some embodiments, Component (B) may be an organic acid that also is an organonitrogen-reactive compound. For example, acrylic acid may serve as both an organic co-monomer and an organonitrogen-reactive compound.

Additionally, organosilanes or organopolysiloxanes having organonitrogen-reactive groups can be suitable for Component (E). Such compounds include, but are not limited to, 3-isocyanatopropyltrimethoxysilane; 3-glycidoxypropyltrimethoxysilane; propylsuccinic anhydride functionalized linear, branched, resinous, and hyperbranched organopolysiloxanes; cyclohexenyl anhydride functional linear, resinous, and hyperbranched organopolysiloxanes; carboxylic acid functionalized linear, branched, resinous, and hyperbranched organopolysiloxanes such as carboxydecyl terminated oligomeric or polymeric polydimethylsiloxanes; and aldehyde functionalized linear, branched, resinous, and hyperbranched organopolysiloxanes such as undecylenic aldehyde-terminated oligomeric or polymeric polydimethylsiloxanes.

Other suitable organonitrogen-reactive compounds for Component (E) are silicon containing compounds that, when exposed to moisture, release an acid that causes the organoborane-organonitrogen complex of Component (C) to disassociate. Such compounds include, but are not limited to, halo silanes, acid anhydride (carboxylic acid) siloxanes, acetoxy siloxanes (such as ethylriacetoxysiloxane and methyl triacetoxysiloxane), alkyl silicic acids, esters of carboxylic acids and silanols, acid chloride siloxanes.

Further examples of compounds that can be useful for Component (E) are those capable of generating organonitrogen-reactive groups when exposed to ultraviolet radiation, such as iodonium salts containing $[SbF_6]^-$ counterions. With such compounds, it may be useful to also include a photosensitizing compound such as isopropylthioxanthone.

One of skill in the art will recognize that the selection of the organonitrogen-reactive compound for Component (E) will depend upon, among other things, the nature of Component (C). Good results have been obtained with the selection of acetic acid, acrylic acid, isophorone diisocyanate, and carboxyl-terminated polydimethylsiloxanes as Component (E).

When an organonitrogen-reactive compound is used in the silicone composition, free radical generation requires the presence of oxygen. In some embodiments, merely exposing the organonitrogen-reactive compound or the composition containing the organonitrogen-reactive compound to air is sufficient to induce polymerization. In some embodiments, the oxygen dissolved in one or more of the other components of the composition is sufficient. In some embodiments, limiting the concentration of oxygen (but not precluding it from the system) such as by the use of a nitrogen sweep or purge may be advantageous for safety (reduced flammability of volatile fluids), for reaction efficiency, or both. To prevent pre-mature polymerization in the presence of oxygen, Component (C) and Component (E) may be physically or chemically isolated until just prior to the desired time to initiate polymerization and/or crosslinking reactions. For example, the composition may be prepared initially as two separate solutions that are combined into one, just prior to the initiation of polymerization and/or crosslinking. The remaining components of the composition may be distributed in any manner between the two solutions, as long as Component (C) and Component (E) do not contact each other. For example, a first solution comprising Components (A) and (C), and a second solution comprising components (B) and (E) are air stable, but polymerize to form fine particles when the solutions are mixed together in presence of air. Alternatively, components (C) and (E), or both, can be encapsulated or delivered in separate phases. For example, one or both of the Components (C) and (E) can be introduced into the silicone composition in a solid form that prevents their intimate mixing. Polymerization of the composition can be activated by (a) heating it above the softening temperature of the solid phase component or encapsulant, or (b) by the introduction of a solubilizing agent that allows mixing of components (C) and (E). Alternatively, Components (C) and (E) can be combined and packaged anaerobically in a single container, and polymerization can be initiated by introduction of oxygen to the composition.

In some embodiments, an optional organonitrogen-reactive compound is not a component of the silicone composition. In such cases, free radical polymerization may be initiated by exposing the organoborane compound to air, by thermal activation, or via radiation. In the case of thermal activation, the temperature to which the one or more components of the composition must be heated to initiate polymerization is dictated by the nature of the organoborane compound selected as Component (C). For example, if an organoborane-organonitrogen complex is selected as Component (C), the binding energy of the complex will dictate the temperature to which the composition must be heated to initiate dissociation of the complex and polymerization. In some embodiments, Component (C) may be heated prior to its introduction with the other components of the composition. In some embodiments, Component (C) and at least one other component are heated prior to the introduction of any remaining components of the composition.

Optional Component (F), Active Ingredient

Generally, optional Component (F) comprises at least one personal care or healthcare active ingredient that can be added to the silicone composition for in situ encapsulation by the elastomer particles. In some embodiments, Component (F) may be added to the silicone composition during the making of the silicone elastomer (pre-load method) or may be added after formation of the silicone elastomer (post-load method). In some embodiments, thermally-sensitive active ingredients are incorporated into the composition at temperatures below their threshold temperature for thermal response or decomposition. In some embodiments, the active ingredient suspended in the composition can be, but is not required to be, in particulate form. When the active ingredient is in particulate form at the conditions of encapsulation, its particle size, distribution, or shape is not limited. By careful selection of the other components in the composition, the properties of the polymer particle may be controlled to allow a desirable mechanism of release of the active ingredient. Examples of release mechanisms include extraction, dissolution, swelling, melting, softening, degradation, abrading, squeezing or cracking via thermal, mechanical, and chemical stress.

The amount of Component (F) present in the silicone composition may vary, but in some embodiments ranges from about 0% to about 50% (by weight), alternatively from about 1% to about 25% (by weight), alternatively from about 1% to about 10% (by weight), based on the amount by total weight of components (A)-(E) in the silicone composition.

As used herein, a "personal care or healthcare active ingredient" means any compound or mixtures of compounds that are known in the art as additives in the personal care formulations that are typically added for the purpose of treating hair or skin to provide a cosmetic and/or aesthetic benefit; any compound or mixtures of compounds that are known in the art to provide a pharmaceutical or medical benefit; any compound that is intended to furnish pharmacological activity or other direct effect in the diagnosis, cure, mitigation, treatment, or prevention of disease, or to affect the structure or any function of the body of a human or other animals; and any compound that may undergo chemical change in the manufacture of drug products and be present in drug products in a modified form intended to furnish the specified activity or effect. Thus, "personal care and healthcare active ingredient" includes, but is not limited to, an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Some representative examples of personal care and healthcare active ingredients include, but are not limited to, drugs; vitamins; proteins; fragrances or perfumes; plant extracts; minerals; hormones; topical antimicrobial agents such as antibiotic active ingredients; antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

In some embodiments, active ingredients suitable for Component (F) include both fat or oil-soluble vitamins, as well as water-soluble vitamins. Oil-soluble vitamins useful as Component (F) include, but are not limited to, Vitamin A1, RETINOL, C2-C18 esters of RETINOL, vitamin E, TOCOPHEROL, esters of vitamin E, and mixtures thereof. RETINOL includes trans-RETINOL, 1,3-cis-RETINOL, 11-cis-RETINOL, 9-cis-RETINOL, and 3,4-didehydro-RETINOL. It should be noted that RETINOL is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, a-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Water-soluble vitamins useful as Component (F) include, but are not limited to, Vitamin C, Vitamin B1, Vitamin B2, Vitamin B6, Vitamin B12, niacin, folic acid, biotin, and pantothenic acid. Other suitable water-soluble vitamins and the INCI names for the vitamins considered included herein are ASCORBYL DIPALMITATE, ASCORBYL METHYLSILANOL PECTINATE, ASCORBYL PALMITATE, and ASCORBYL STEARATE.

Some examples of commercially available products suitable for use as Component (F) are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

In some embodiments, the personal care or healthcare active ingredient used as Component (F) can be a water-soluble or an oil-soluble active drug ingredient. Representative examples of some suitable water-soluble active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, and mebendazole.

Representative examples of some suitable oil-soluble active drug ingredients which can be used as Component (F) are clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anaesthetic agents such as lidocaine; antipruritic agents; antidermatitis agents; and agents generally considered barrier films.

In some embodiments, component (F) can also be a protein, such as an enzyme. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases and mixtures thereof.

In some embodiments, component (F) may be a sunscreen agent. The sunscreen agent can be selected from any sunscreen agent known in the art to protect skin from the harmful effects of exposure to sunlight. The sunscreen can be an organic compound, an inorganic compound, or mixtures thereof. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate 0, Phenylbenzimidazole Sulfonic Acid, Red Petrolatum, Sulisobenzone, Titanium Dioxide, and Trolamine Salicylate.

The organic sunscreen compound is typically chosen from an organic compound that absorbs ultraviolet (UV) light. Some examples of UV light absorbing compounds are Acetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycin namate, Dibenzoxazol Naphthalene, Di-t-Butyl Hydroxybenzyl idene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, TriPABA Panthenol, Urocanic Acid, and VA/Crotonates/Methacryloxybenzophenone copolymer.

Alternatively, the sunscreen agent is a cinnamate based organic compound, or alternatively, the sunscreen agent is octyl methoxycinnamate, such as Uvinul® MC 80 an ester of para-methoxycinnamic acid and 2-ethylhexanol.

In some embodiments, Component (F) may be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulphur containing compounds, as well as essential oils of natural or synthetic origin. Many of these perfume ingredients are described in detail in standard textbook references such as Perfume and Flavour Chemicals, 1969, S. Arctander, Montclair, N.J.

Fragrances may be exemplified by, but not limited to, perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethylCyclohexanone Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-Indanone 4-Damascol, Dulcinyl or Cassione, Gelsone, Hexylon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran.

More preferably, the perfume ketones are selected for its odor character from Alpha Damascone, Delta Damascone, Iso Damascone, Carvone, Gamma-Methyl-Ionone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odour character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cm namic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.O(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carboxaldehyde, 5 or 6 methoxyl 0 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butena I, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

More preferred aldehydes are selected for their odour character from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

In some embodiments, Component (F) may be one or more plant extracts. Examples of these components are as follows: Ashitaba extract, avocado extract, hydrangea extract, Althea extract, Arnica extract, aloe extract, apricot extract, apricot kernel extract, Ginkgo Biloba extract, fennel extract, turmeric [Curcuma] extract, oolong tea extract, rose fruit extract, Echinacea extract, Scutellaria root extract, Phellodendro bark extract, Japanese Coptis extract. Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, Pyracantha Fortuneana Fruit extract, Kiwi extract, Cinchona extract, cucumber extract, guanocine. Gardenia extract, Sasa Albo-marginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, Salvia extract, Saponaria extract, Bamboo extract, Crataegus fruit extract, Zanthoxylum fruit extract, shiitake extract, Rehmannia root extract, gromwell extract. Perilla extract, linden extract, Filipendula extract, peony extract, Calamus Root extract, white birch extract, Horsetail extract, Hedera Helix (Ivy) extract, hawthorn extract, Sambucus nigra extract, Achillea millefolium extract, Mentha piperita extract, sage extract, mallow extract, Cnidium officinale Root extract, Japanese green gentian extract, soybean extract, jujube extract, thyme extract, tea extract, clove extract, Gramineae imperata cyrillo extract, Citrus unshiu peel extract Japanese Angellica Root extract, Calendula extract, Peach Kernel extract, Bitter orange peel extract, Houttuyna cordata extract, tomato extract, natto extract, Ginseng extract, Green tea extract (camelliea sinesis), garlic extract, wild rose extract, hibiscus extract, Ophiopogon tuber extarct, Nelumbo nucifera extract, parsley extract, honey, hamamelis extract, Parietaria extract, Isodonis herba extract, bisabolol extract, Loquat extract, coltsfoot extract, butterbur extract, Porid cocos wolf extract, extract of butcher's broom, grape extract, propolis extract, luffa extract, safflower extract, peppermint extract, linden tree extract, Paeonia extract, hop extract, pine tree extract, horse chestnut extract, Mizu-bashou extract, Mukurossi peel extract, Melissa extract, peach extract, cornflower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, and royal jelly extract.

In some embodiments, Component (F) is a personal care or health care active ingredient selected from vitamins, sunscreens, plant extracts, fragrances or perfumes, topical drug actives, proteins (including, but not limited to enzymes), antiperspirants, deodorants, moisturizers, antifungal agents, and antimicrobial agents.

Optional Component (G), Emulsifier

Generally, optional Component (G) comprises at least one emulsifier that can be added to the silicone composition for emulsification of the elastomer particles. As used herein, "emulsifier" refers to any compound or substance that enables the formation of an emulsion. The emulsion may be an oil/water emulsion, a water/oil emulsion, a multiple phase or triple emulsion. The emulsifier may be selected from any surface active compound or polymer capable of stabilizing emulsions. Typically, such surface active compounds or polymers stabilize emulsions by preventing coalescence of the dispersed particles. The surface active compounds useful as emulsifiers in the present process may be a surfactant or combination of surfactants. In principle, the surfactant used can be any surfactant known for emulsification of silicones and can be cationic, anionic, nonionic, and/or amphoteric.

Examples of cationic surfactants include, but are not limited to, quaternary ammonium hydroxides such as octyl trimethyl ammonium hydroxide, dodecyl trimethyl ammonium hydroxide, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, tallow trimethyl ammonium hydroxide and coco trimethyl ammonium hydroxide as well as corresponding salts of these materials, fatty amines and fatty acid amides and their derivatives, basic pyridinium compounds, and quaternary ammonium bases of benzimidazolines and poly(ethoxylated/propoxylated) amines.

Examples of anionic surfactants include, but are not limited to, alkyl sulphates such as lauryl sulphate, polymers such as acrylates/$C_{10-30}$ alkyl acrylate crosspolymer alkylbenzenesulfonic acids and salts such as hexylbenzenesulfonic acid, octylbenzenesulfonic acid, decylbenzenesulfonic acid, dodecylbenzenesulfonic acid, cetylbenzenesulfonic acid and myristylbenzenesulfonic acid; the sulphate esters of monoalkyl polyoxyethylene ethers; alkylnapthylsulfonic acid; alkali metal sulfoccinates, sulfonated glyceryl esters of fatty acids such as sulfonated monoglycerides of coconut oil acids, salts of sulfonated monovalent alcohol esters, amides of amino sulfonic acids, sulfonated products of fatty acid nitriles, sulfonated aromatic hydrocarbons, condensation products of naphthalene sulfonic acids with formaldehyde, sodium octahydroanthracene sulfonate, alkali metal alkyl sulphates, ester sulphates, and alkarylsulfonates. Anionic surfactants include alkali metal soaps of higher fatty acids, alkylaryl sulfonates such as sodium dodecyl benzene sulfonate, long chain fatty alcohol sulfates, olefin sulfates and olefin sulfonates, sulfated monoglycerides, sulfated esters, sulfonated ethoxylated alcohols, sulfosuccinates, alkane sulfonates, phosphate esters, alkyl isethionates, alkyl taurates, and alkyl sarcosinates.

Examples of non-ionic surfactants include, but are not limited to, condensates of ethylene oxide with long chain fatty alcohols or fatty acids such as a C12-C16 alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, fatty amine oxides, polyoxyalkylene alkyl ethers such as polyethylene glycol long chain alkyl ether, polyoxyalkylene sorbitan ethers, polyoxyalkylene alkoxylate esters, polyoxyalkylene alkylphenol ethers, ethylene glycol propylene glycol copolymers and alkylpolysaccharides, polymeric surfactants such as polyvinyl alcohol (PVA) and polyvinylmethylether. In certain embodiments, the surfactant is a polyoxyethylene fatty alcohol or mixture of polyoxyethylene fatty alcohols. In other embodiments, the surfactant is an aqueous dispersion of a polyoxyethylene fatty alcohol or mixture of polyoxyethylene fatty alcohols.

Examples of amphoteric surfactants include cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds.

The surfactant can be aqueous, non-aqueous, and/or in diluted or undiluted form. Thus, the surfactant chosen, its aqueous/non-aqueous nature, its diluted/undiluted form, and the desired properties of the emulsion will dictate whether or not additional water is added in order to form the emulsion.

In alternative embodiments, the emulsifier may be a polymer or those materials considered in the art as "thickeners" or "thickening agents." Such polymeric emulsifiers include, but are not limited to, polyvinyl alcohol, cellulosic polymers or xanthan gums. The polyvinyl alcohol includes hydrolyzed polyvinyl alcohols, such as 80-95% hydrolyzed polyvinyl alcohol. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by carboxy methylcellulose, methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or mixtures of 2 or more of these. Typically the thickening agent is selected from the group consisting of cellulose derivatives, saccharide derivatives, and electrolytes, or from a combination of two or more of the above thickening agents exemplified by a combination of a cellulose derivative and any electrolyte, and a starch derivative and any electrolyte.

While numerous emulsifiers are suitable as Component (G), good results have been obtained with the selection of secondary alcohol ethoxylates such as Tergitol™ 15-s-3, Tergitol™ 15-s-40, polyglycol-modified siloxanes, polyglycol-modified trimethylsilylated silicates, ethoxylated quaternary ammonium salt solutions, and cetyltrimethylammonium chloride solutions.

Additional Optional Components

The silicone compositions can also include additional components. Without limitation, examples of such optional additional components include surfactants; emulsifiers; dispersants; polymeric stabilizers; crosslinking agents; combinations of polymers, crosslinking agents, and catalysts useful for providing a secondary polymerization or crosslinking of the particles; rheology modifiers such as thickeners; density modifiers; aziridine stabilizers; cure modifiers such as hydroquinone and hindered amines; free radical initiators such as organic peroxides and ozonides; polymers; diluents; acid acceptors; antioxidants; heat stabilizers; flame retardants; scavenging agents; silylating agents; foam stabilizers; solvents; diluents; plasticizers; fillers and inorganic particles, pigments, dyes and dessicants.

Compositions according to the invention may contain a number of optional components selected from those known in the state of the art to be ingredients in personal and healthcare formulations. Illustrative, non-limiting examples include surfactants, solvents, powders, coloring agents, thickeners, waxes, stabilizing agents, pH regulators, and silicones.

Thickening agents may optionally be added to the aqueous phase of the compositions to provide a convenient viscosity. For example, viscosities within the range of 500 to 25,000 mm$^2$/s at 25° C. or more, alternatively in the range of 3,000 to 7,000 mm$^2$/s at 25° C., are usually suitable. Suitable thickening agents are exemplified by sodium alginate; gum arabic; polyoxyethylene; guar gum; hydroxypropyl guar gum; ethoxylated alcohols, such as laureth-4 or polyethylene glycol 400; cellulose derivatives exemplified by methylcellulose, methylhydroxypropylcellulose, hydroxypropylcellulose, polypropylhydroxyethylcellulose; starch and starch derivatives exemplified by hydroxyethylamylose and starch amylose; locust bean gum; electrolytes exemplified by sodium chloride and ammonium chloride; saccharides such as fructose and glucose; and derivatives of saccharides such as PEG-120, methyl glucose diolate; or mixtures of two or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent may be present in shampoo compositions of the present invention in an amount sufficient to provide a viscosity in the final shampoo composition of from 500 to 25,000 mm$^2$/s. The thickening agent may be present in an amount from about 0.05 to 10 wt %; alternatively from about 0.05 to 5 wt %, based on the total weight of the composition. Thickeners based on acrylate derivatives, such as polyacrylate crosspolymer, Acrylates/C1030 Alkyl Acrylate crosspolymer, polyacrylamide derivatives, sodium polyacrylate may also be added.

Stabilizing agents may optionally be used in the water phase of compositions of the present invention. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to about 0.1 to 5 wt % and more alternatively 0.5 to 3 wt % of the total composition. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xantham gum.

Other optional components can include powders and pigments especially when the composition according to the invention is intended to be used for make-up. The powder component of the invention can be generally defined as dry, particulate matter having a particle size of 0.02-50 microns. The particulate matter may be colored or non-colored (for example white). Suitable powders include, but are not limited to, bismuth oxychloride, titanated mica, fumed silica, spherical silica beads, polymethylmethacrylate beads, boron nitride, aluminum silicate, aluminum starch octenylsuccinate, bentonite, kaolin, magnesium aluminum silicate, silica, silica silylate, talc, mica, titanium dioxide, nylon, silk powder. The above-mentioned powders may be surface treated to render the particles hydrophobic in nature. The powder component also comprises various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent colouring agent, such as carbon black, chromium or iron oxides, ultramarines, manganese pyrophosphate, iron blue, and titanium dioxide, pearlescent agents, generally used as a mixture with coloured pigments, or some organic dyes, generally used as a mixture with coloured pigments and commonly used in the cosmetics industry, can be added to the composition. In general, these colouring agents can be present in an amount by weight from 0 to 20% with respect to the weight of the final composition.

Pulverulent inorganic or organic fillers can also be added, generally in an amount by weight from 0 to 40% with respect to the weight of the final composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked, copolymer microspheres such as EXPANCEL (Nobel Industrie), polytrap and silicone resin microbeads (TOSPEARL from Toshiba, for example).

Waxes or wax-like materials may be optional components of compositions of the present invention, wherein such components generally have a melting point range of 35 to 120° C. at atmospheric pressure. Waxes in this category include synthetic wax, ceresin, paraffin, ozokerite, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, soy waxes or mixtures thereof. Mention may be made, among the waxes capable of being used as non-silicone fatty substances, of animal waxes, such as beeswax; vegetable waxes, such as carnauba, candelilla wax, mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

Optional components may also include silicones (including any already described), organofunctional siloxanes, alkylmethylsiloxanes, siloxane resins and silicone gums. Alkylmethylsiloxanes useful for compositions of the present invention may have the formula $Me_3SiO[Me_2SiO]_y[MeRSiO]_zSiMe_3$, in which R is a hydrocarbon group containing 6-30 carbon atoms, Me represents methyl, and the degree of polymerization (DP), i.e., the sum of y and z is 3-50. Both the volatile and liquid species of alkymethysiloxanes can be used in the composition. Phenyl functional siloxanes may also be added such as Dow Corning® 556 Fluid.

Silicone gums may also be optional components of compositions of the present invention. Polydiorganosiloxane gums are known in the art and are available commercially. They consist of generally insoluble polydiorganosiloxanes having a viscosity in excess of 1,000,000 centistoke ($mm^2/s$) at 25° C., alternatively greater than 5,000,000 centistoke ($mm^2/s$) at 25° C. These silicone gums are typically sold as compositions already dispersed in a suitable solvent to facilitate their handling. Ultra-high viscosity silicones [those typically having a kinematic viscosity from about 5 million centistoke ($mm^2/s$) at 25° C., to about 20 million centistoke ($mm^2/s$) at 25° C.] can also be included as optional components. In some embodiments, compositions of this type may be in the form of suspensions.

Silicone resins may also be optional components in compositions of the present invention. Such resins are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for use are generally supplied in an unhardened form in low viscosity volatile or nonvolatile silicone fluids, and may be incorporated into compositions of the present invention in their non-hardened forms rather than as hardened resinous structures.

Silicone carbinol fluids may also be optional components. These materials are described in WO 03/101,412 A2, and can be commonly described as substituted hydrocarbyl functional siloxane fluids or resins.

Water soluble or water dispersible silicone polyether compositions may also be optional components. These are also known as polyalkylene oxide silicone copolymers, silicone poly(oxyalkylene) copolymers, silicone glycol copolymers, or silicone surfactants. These can be linear rake or graft type materials, ABA or ABn type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible.

Compositions according to the present invention can be used in o/w, s/w, w/o, w/s, and non-aqueous o/o, o/s, and s/o emulsions or multiple phase emulsions using silicone emulsifiers. Typically the water-in-silicone emulsifier in such formulation is non-ionic and is selected from polyoxyalkylene-substituted silicones (rake or ABn type), silicone alkanolamides, silicone esters and silicone glycosides. Suitable silicone-based surfactants are well known in the art, and have been described for example in U.S. Pat. No. 4,122,029 (Gee et al.), U.S. Pat. No. 5,387,417 (Rentsch), and U.S. Pat. No. 5,811,487 (Schulz et al), JP 2001-294512.

When a composition according to the invention is an oil-in-water emulsion, it will include common ingredients generally used for preparing emulsions such as but not limited to non ionic surfactants well known in the art to prepare o/w emulsions. Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

The composition according to the invention can also be under the form of aerosols in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Hydrophilically-Modified Silicone Microparticles and Pastes

According to various embodiments of the invention, provided are organopolysiloxane/hydrophilic organic co-polymer microparticles, silicone pastes comprising such microparticles, and methods of making the same. In some embodiments, silicone pastes can be prepared by a method comprising: (I) forming a reaction mixture comprising Component (A), at least one organopolysiloxane having an average of at least two free radical polymerizable groups per molecule; Component (B), at least one free radical polymerizable organic co-monomer having at least one hydrophilic group per molecule; Component (C), at least one organoborane free radical initiator; Component (D), at least one non-solvent that is immiscible with Component (A); optionally Component (E), at least one organonitrogen-reactive compound; optionally Component (F), at least one active ingredient suitable for use in personal care and healthcare products; and optionally Component (G), at least one emulsifier; (II) agitating the reaction mixture in the presence of oxygen while maintaining the temperature at from about 5° C. to about 95° C.; wherein agitation occurs during combination of the components, after combination of the components, or combinations thereof; and (III) allowing polymerization and cross-linking reactions to occur until water insoluble silicone microparticles having hydrophilic functionality are formed. The microparticles can be dispersed in at least one absorbable fluid to form a paste having silicone microparticles that are swollen with the fluid. In some embodiments, the swollen particles are substantially spherical. The silicone pastes may also comprise at least one active ingredient incorporated into the elastomer particles, and in some embodiments, the compositions are formed at room temperature to allow in situ incorporation of thermally-sensitive active ingredients. Silicone pastes of the provided methods are stable and can have a wide range of viscosities, thereby making them particularly useful as bases for personal care (such as cosmetics) and healthcare products. Such pastes are typically characterized as having pleasant sensory properties, thixotropy, and shear thinning. In some embodiments, the silicone paste compositions comprise from about 5% to about 50% (by weight) of elastomer; alternatively, from about 10% to about 30% (by weight) of elastomer. In some embodiments, the silicone paste compositions have a viscosity of at least 25 Pa·s, alternatively at least 40 Pa·s, alternatively at least 100 Pa·s. In some embodiments, the pastes have a viscosity of from about 25 Pa·s to about 100 Pa·s. In some embodiments, the pastes have a viscosity of from about 25 Pa·s to about 40 Pa·s. In some embodiments, the pastes have a viscosity of from about 40 Pa·s to about 100 Pa·s. In some embodiments, the pastes have a viscosity greater than 100 Pa·s.

In some embodiments, the silicone paste compositions have substantially spherical swollen silicone elastomeric microparticles with an average diameter of from about 0.1 μm to about 500 μm.

In some embodiments, agitation of the components is continued until the composition is formed. In some embodiments, agitation occurs only to initiate the reaction and then is discontinued.

In some embodiments, agitation of the components occurs in the presence of oxygen while maintaining the temperature at from about 5° C. to about 95° C. Thus, temperature may be from about 5° C. to about 10° C., from about 10° C. to about 15° C., from about 15° C. to about 20° C., from about 20° C. to about 25° C., from about 25° C. to about 30° C., from about 30° C. to about 35° C., from about 35° C. to about 40° C., from about 40° C. to about 45° C., from about 45° C. to about 50° C., from about 50° C. to about 55° C., from about 55° C. to about 60° C., from about 60° C. to about 65° C., from about 65° C. to about 70° C., from about 70° C. to about 75° C., from about 75° C. to about 80° C., from about 80° C. to about 85° C., from about 85° C. to about 90° C., and from about 90° C. to about 95° C. In some embodiments, agitation occurs in the presence of oxygen while maintaining the temperature at from about 10° C. to about 35° C. Thus, the temperature may be 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., and 35° C.

In some embodiments, the described method is an emulsion polymerization process wherein a phase comprising Components (A), (B) and (C) is dispersed in a continuous phase comprising Component (D) and wherein, when shear is applied, an oil-in-water emulsion is formed that, when a Component (E) compound (such is as acids, isocyanates and epoxides) is added, precipitation of insoluble polymer microparticles occurs.

In some embodiments, the described method is an emulsion polymerization process wherein a phase comprising Components (A), (B) and (C) is dispersed in a continuous phase comprising Component (D) and wherein, when shear is applied, an oil-in-water emulsion is formed that, when acidified, causes precipitation of insoluble polymer microparticles.

Absorbable Fluid

According to various embodiments of the invention, the silicone elastomers formed by the free radical polymerization and cross-linking reactions are insoluble in Component (D), but when dispersed in certain fluids, the elastomers absorb the fluid to form swollen particles. Accordingly, an "absorbable fluid" is intended to mean a fluid that is absorbable by silicone elastomers of the invention. In some embodiments, an absorbable fluid may also act as a solvent for the elastomers. In some embodiments, an absorbable fluid may be immiscible with water.

In some embodiments, suitable absorbable fluids may be selected from silicones; organic compounds; and "ecologically-friendly" solvents, such as ionic liquids and supercritical fluids; and mixtures thereof.

Examples of suitable silicones for an absorbable fluid include, but are not limited to, low molecular weight linear or cyclic volatile silicones; non-volatile alkyl or aryl silicones; and low molecular weight linear or cyclic functional silicones. The silicone miscible fluid may be a single silicone or a mixture of silicones. In some embodiments, an absorbable fluid is a low molecular weight volatile methyl silicone (VMS) having an average unit formula of $(CH3)_xSiO_{(4-x)/2}$ in which x has an average value of from 2 to 3. Representative units in such VMS compounds are $(CH_3)_3SiO_{1/2}$ units and $(CH_3)_2SiO_{2/2}$ units, and there additionally may be $CH_3SiO_{3/2}$ units and/or $SiO_{4/2}$ units that result in the formation of branched linear or cyclic volatile methyl silicones. Linear VMS have the formula $(CH_3)_3SiO\{(CH_3)_2SiO\}_ySi(CH_3)_3$ where y is 0 to 5. Cyclic VMS have the formula $\{(CH_3)_2SiO\}_z$ where z is 3 to 6. Typically these volatile methyl silicones have boiling points less than about 250° C. and viscosities of from about 0.65 to 5.0 centistokes (mm²/s).

In some embodiments, suitable silicones include, but are not limited to, linear volatile methyl silicones, such as hexamethyldisiloxane, octamethyltrisiloxane, decamethyltetrasiloxane, dodecamethylpentasiloxane, tetradecamethylhexasioxane, and hexadecamethylheptasiloxane; cyclic volatile methyl silicones, such as hexamethylcyclotrisiloxane, octamethylcyclotetrasiloxane, decamethylcyclopentasiloxane, and dodecamethylcyclohexasiloxane; and branched volatile methyl silicones, such as heptamethyl-3-{(trimethylsilyl)oxy}trisiloxane, hexamethyl-3,3, bis{(trimethylsilyl)oxy}trisiloxane, and pentamethyl {(trimethylsilyl)oxycyclotrisiloxane.

In some embodiments, non-volatile alkyl or aryl silicones include, but are not limited to, linear poly alkyl or aryl silicones, such as compounds of the formula $R^4{}_3SiO(R^4{}_2SiO)_m SiR^4{}_3$; and cyclic poly alkyl or aryl silicones, such as compounds of the formula $(R^4{}_2SiO)_n$; wherein $R^4$ is an alkyl group of 1 to 6 carbon atoms, or an aryl group such as phenyl, m has a value of 0 to 80, preferably 0 to 20 and n has a value of 0 to 9, preferably 4 to 6. These silicones have viscosities generally in the range of about 1 to 100 centistokes (mm²/s). Other representative low molecular weight non-volatile silicones have the general structure $R^5{}_3SiO(R^5R^6SiO)_p SiR^5{}_3$ where p has a value to provide polymers with a viscosity in the range of about 100 to 10,000 centistokes (mm²/sec) and $R^5$ and $R^6$ are alkyl radicals of 1 to 30 carbon atoms, or an aryl group such as phenyl. Typically, the value of p is about 60 to 600. Non-volatile polysiloxanes may be exemplified by, but are not limited to, polydimethylsiloxane, polydiethylsiloxane, polymethylethylsiloxane, polymethylphenylsiloxane, and polydiphenylsiloxane.

In some embodiments, low molecular weight functional silicones can be represented by acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

In some embodiments, an absorbable fluid may be selected from organic compounds. Examples include, but are not limited to, aromatic hydrocarbons; aliphatic hydrocarbons; alcohols; aldehydes; ketones; amines; esters; ethers; glycols; glycol ethers; alkyl halides; or aromatic halides. The organic miscible fluids may be further exemplified as alcohols, such as methanol, ethanol, 1-propanol, cyclohexanol, benzyl alcohol, 2-octanol, ethylene glycol, propylene glycol, and glycerol; aliphatic hydrocarbons, such as pentane, cyclohexane, heptane, VM&P solvent, and mineral spirits; alkyl halides, such as chloroform, carbon tetrachloride, perchloroethylene, ethyl chloride, and chlorobenzene; amines, such as isopropylamine, cyclohexylamine, ethanolamine, and diethanolamine; aromatic hydrocarbons, such as benzene, toluene, ethylbenzene, and xylene; esters, such as ethyl acetate, isopropyl acetate, ethyl acetoacetate, amyl acetate, isobutyl isobutyrate, and benzyl acetate; ethers, such as ethyl ether, o-butyl ether, tetrahydrofuran, and 1,4-dioxane; glycol ethers, such as ethylene glycol monomethyl ether, ethylene glycol monomethyl ether acetate, diethylene glycol monobutyl ether, and propylene glycol monophenyl ether; ketones, such as acetone, methyl ethyl ketone, cyclohexanone, diacetone alcohol, methyl amyl ketone, and diisobutyl ketone; petroleum hydrocarbons, such as gasoline, naphtha, kerosene, gas oil, heavy oil, and crude oil; lubricating oils such as spindle oil and turbine oil; and organic oils.

When an absorbable fluid is an organic oil, it may be selected from any organic oils known in the art suitable for use in the preparation of personal, household, or healthcare formulations. Suitable organic oils include, but are not limited to, natural oils such as coconut oil, corn oil, soybean oil, olive oil, rape seed oil, cotton seed oil, sardine oil, herring oil, and whale oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate. The organic oil components can also be mixture of low viscosity and high viscosity oils. Suitable low viscosity oils have a viscosity of 5 to 100 mPas at 25° C., and are generally esters having the structure RCO—OR' wherein RCO represents the carboxylic acid radical and wherein OR' is an alcohol residue. Examples of suitable low viscosity oils include, but are not limited to, isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof.

Suitable high viscosity oils generally have a viscosity of 200-1,000,000 mPas at 25° C., alternatively a viscosity of 100,000-250,000 mPas. Examples of suitable high viscosity oils include, but are not limited to, castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof.

Other organic compounds suitable for an absorbable fluid include, but are not limited to, mineral oils such as liquid paraffin or liquid petroleum; animal oils such as perhydrosqualene oil; vegetable oils such as sweet almond, calophyllum, palm, castor, avocado, jojoba, olive or cereal germ oil; esters of lanolic acid, oleic acid, lauric acid, stearic acid or myristic acid; alcohols such as oleyl alcohol, linoleyl or linolenyl alcohol, isostearyl alcohol or octyldodecanol; and acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The organic oil may also be a volatile organic solvent. Suitable as a volatile organic solvent component are various C8-C20 isoparaffins such as C12 isoparaffin made by The Permethyl Corporation having the tradename Permethyl® 99A, or a C12 isoparaffin (isododecane). Various C16 isoparaffins commercially available, such as isohexadecane are also suitable. Other suitable volatile solvents are various fluoro containing materials such as Ethyl Perfluoroisobutyl Ether (and) Ethyl Perfluorobutyl Ether (3M Cosmetic fluid CF-76) and Cosmetic Fluid CF-61: Methyl Perfluoroisobutyl Ether (and) Methyl Perfluorobutyl Ether (3M Cosmetic Fluid CF-61).

The organic compound may also be selected from acetonitrile, nitromethane, dimethylformamide, propylene oxide, trioctyl phosphate, butyrolactone, furfural, pine oil, turpentine, and m-creosol; volatile flavoring agents; and other useful flavoring agents including aldehydes and esters; volatile fragrances such as natural products and perfume oils. The organic miscible fluid can be a single compound or a mixture of compounds. Additionally, an absorbable fluid can be a mixture of an organic miscible fluid and other miscible fluids, such as a siloxane.

In some embodiments, an absorbable fluid may be an ionic fluid. Examples of suitable ionic fluids include, but are not limited to, imidazolium derivatives, such as 1-ethyl-3-methylimidazolium tosylate, 1-ethyl-3-methylimidazolium tetrafluoroborate, 1-methyl-3-octylimidazolium chloride, 1-ethenyl-3-ethyl-imidazolium hexafluorophosphate, 1-butyl-3-methylimidazolium hexafluorophosphate; and pyridinium derivatives, such as 1-butyl-4-methylpyridinium chloride, 1-butyl-4-methylpyridinium hexafluorophosphate, and 1-butyl-4-methylpyridinium tetrafluoroborate.

In some embodiments, an absorbable fluid may be a supercritical fluid. Examples of suitable supercritical fluids include, but are not limited to, supercritical carbon dioxide, supercritical water, supercritical ethane, supercritical nitrous oxide, supercritical ammonia; supercritical 1,1,1,2-tetrafluoroethane; supercritical difluoromethane; supercritical pentafluoroethane; and mixtures thereof. The solvent strength of supercritical fluids may also be modified by any number of co-solvents such as methanol, ethanol, acetone, hexane, or benzene.

Examples of a suitable absorbable fluid for the polymerization of radical-polymerizable polydimethylsiloxanes include, but are not limited to, hexane, cyclohexane, heptane, hexamethyldisiloxane, octamethyltrisiloxane, octamethylcyclotetrasiloxane, decamethylcyclopentasiloxane, decamethyltetrasiloxane, isododecane, isohexadecane, isodecylneopentanoate, isononyl isononanoate, isoparaffin, isoalkane, and capryllylmethyl trisiloxane, toluene, ethyl acetate, 1-ethenyl-3-ethyl-imidazolium hexafluorophosphate, tetrapropyl-ammonium tetracyanoborate, and trimethylsilyl-terminated polydimethylsiloxane fluids having a viscosity of less than 1000 cP at 25° C., or a mixture thereof. In some embodiments, the trimethylsilyl-terminated polydimethylsiloxane fluids chosen as an absorbable fluid have a viscosity of from about 0.5 to about 100 cP at 25° C.

While numerous absorbable fluids may be suitable for swelling the silicone polymeric microparticles, good results have been obtained with the selection of linear and cyclic siloxanes such as decamethylcyclopentasiloxane, isododecane, and isohexadecane.

Personal Care and Healthcare Products

Silicone compositions of the present invention may be useful for a variety of applications, such as for personal care and healthcare products. For example, such compositions may be used in deodorants; antiperspirants; antiperspirant/deodorants; shaving products; skin care products such as lotions, moisturizers, and toners; bath products; cleansing products; hair care products such as shampoos, conditioners, mousses, styling gels, hair sprays, hair dyes, hair color products, hair bleaches, waving products, and hair straighteners; manicure products such as nail polish, nail polish remover, nails creams and lotions, and cuticle softeners; protective creams such as sunscreens, insect repellent and anti-aging products; cosmetics such as lipsticks, foundations, face powders, eye liners, eye shadows, blushes, makeup, mascaras; vitamin and hormone carriers; fragrance carriers; and other personal care formulations where silicone components have conventionally been added, as well as drug delivery systems for topical application of medicinal compositions that are to be applied to the skin.

For example, silicone compositions of the invention can be used to improve the properties of skin creams, skin care lotions, moisturizers, facial treatments such as ache or wrinkle removers, personal and facial cleansers, bath oils, perfumes, colognes, sachets, sunscreens, pre-shave and after-shave lotions, liquid soaps, shaving soaps, shaving lathers, hair shampoos, hair conditioners, hair sprays, mousses, permanents, depilatories, cuticle coats, and cosmetics. An example of their use in cosmetics is as leveling and spreading agents for pigments in make-ups, color cosmetics, foundations, blushes, lipsticks, lip balms, eyeliners, mascaras, oil removers, color cosmetic removers, and powders.

In various embodiments, silicone elastomeric pastes of the present invention may be useful in personal care and healthcare products for humans or animals to moisturize, color, to generally improve appearance, or to apply active ingredients, such as sunscreens, deodorants, and insect repellents. For example, they may be useful as thickening agents, as taught in U.S. Pat. No. 6,051,216, U.S. Pat. No. 5,919,441, and U.S. Pat. No. 5,981,680; to structure oils, as disclosed in WO 2004/060271 and WO 2004/060101; in sunscreen compositions as taught in WO 2004/060276; as structuring agents in cosmetic compositions also containing film-forming resins, as disclosed in WO 03/105801; in the cosmetic compositions as taught in US2003/0235553, US2003/0072730, US2003/0170188, EP 1,266,647, EP 1,266,648, EP 1,266,653, WO 03/105789, WO 2004/000247, and WO 03/106614; as structuring agents as taught in WO 2004/054523; in long wearing cosmetic compositions as taught in US2004/0180032: in transparent or translucent care and/or make up compositions as discussed in WO 2004/054524; all of which are incorporated herein by reference.

Silicone elastomeric pastes of the present invention may be useful in anti-perspirant and deodorant products including, but not limited to, in the form of sticks, soft solid, roll on, aerosol, and pump sprays. For example, such anti-perspirant and deodorant products may comprise as active ingredients, aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, and zinc ricinoleate.

Personal care and healthcare products of the present invention may be in the form of a cream, a gel, a powder, a paste, or a freely pourable liquid. Generally, such products can generally be prepared at room temperature if no solid materials at room temperature are present in the products, using simple propeller mixers, Brookfield counter-rotating mixers, or homogenizing mixers. No special equipment or processing conditions are typically required. Depending on the type of form made, the method of preparation will be different, but such methods are well known in the art.

Personal care and healthcare products of the present invention can be used by standard methods, such as applying them to the human body, e.g. skin or hair, using applicators, brushes, applying by hand, pouring them and/or possibly rubbing or massaging the products onto or into the body. Removal methods, for example for color cosmetics are also well known standard methods, including washing, wiping, and peeling. For use on the skin, personal care and healthcare products may be used in a conventional manner, for example for conditioning the skin. An effective amount of the product for the purpose is applied to the skin. Such effective amounts generally range from about 1 mg/cm$^2$ to about 3 mg/cm$^2$. Application to the skin typically includes working the composition into the skin. This method for applying to the skin comprises the steps of contacting the skin with the product in an effective amount and then rubbing the product into the skin. These steps can be repeated as many times as desired to achieve the desired benefit.

For use on hair, personal care and healthcare products may be used in a conventional manner, for example for conditioning hair. An effective amount of the product for the purpose is applied to the hair. Such effective amounts generally range from about 1 g to about 50 g, alternatively from about 1 g to about 20 g. Application to the hair typically includes working the product through the hair such that most or all of the hair is contacted with the product. This method for applying to the hair comprises the steps of contacting the hair with the product in an effective amount and then working the product through the hair. These steps can be repeated as many times as desired to achieve the desired benefit.

In some embodiments, personal care and healthcare products of the present invention are selected from antiperspirants, deodorants, skin creams, skin care lotions, moisturizers, facial treatment products, facial cleansing products, bath oils, perfumes, colognes, sachets, sunscreens, pre-shave lotions, after-shave lotions, liquid soaps, body washes, bar soaps, shaving soaps, shaving lathers, hair shampoos, hair conditioners, hair colorants, hair sprays, mousses, permanents, depilatories, cuticle coats, make-ups, color cosmetics, foundations, blushes lipsticks, lip balms, eyeliners, mascaras, eye shadows, oil removers, and cosmetic removers.

EXAMPLES

The present invention will be better understood by reference to the following examples which are offered by way of illustration and which one of skill in the art will recognize are not meant to be limiting.

Example 1

Isolation of Polymer Microparticles Comprising Methyl Methacrylate Co-Polymer

In a polypropylene cup, 4.75 g methacrylate (α,ω-methacryloxypropyldimethylsiloxy) terminated polydimethylsiloxane (PDMS) having a number average molecular weight (Mn) of 8200 g/mol and polydispersity of about 2.0 (MA-PDMS) was added to 0.26 g methyl methacrylate and 0.15 g of an equimolar triethylborane-propanediamine complex (TEB-PDA) and mixed in a FlackTek SpeedMixer for 15 seconds. To the contents was added 0.08 g Tergitol-15-s-3 with 15 seconds mixing, followed by 0.41 g Tergitol-15-s-40 and mixed for 15 seconds. Then 0.28 g deionized water was added and mixed for 15 s. An additional 20 ml of water was added in 2 ml increments with 15 s mixing after each increment to form an oil-in-water emulsion. Emulsion contents were added drop wise to a solution in a glass jar containing 0.08 g acetic acid and 19.63 g water, causing formation and precipitation of polymer microparticles. The resulting particles were isolated by vacuum filtration using a faucet-based aspirator then oven drying in a vacuum oven with pressure of <25 mm Hg overnight at 25° C. Unless otherwise stated, the same oven drying conditions were used in all subsequent examples.

Example 2

Isolation of Polymer Microparticles Comprising Stearyl Methacrylate Co-Polymer

In a polypropylene cup, 4.77 g MA-PDMS was added to 0.26 g stearyl methacrylate and 0.17 g TEB-PDA and mixed in a FlackTek SpeedMixer for 15 seconds. To the contents was added 0.07 g Tergitol-15-s-3 with 15 seconds mixing, followed by 0.42 g Tergitol-15-s-40 and mixing for 15 seconds. Then 0.29 g deionized water was added and mixed for 15 s. An additional 20 ml of water was added in 2 ml increments each with mixing for 15 s after each increment to form an oil-in-water emulsion. Emulsion contents were added dropwise to a solution in a glass jar containing 0.08 g acetic acid and 19.45 g water, causing formation and precipitation of polymer microparticles. The resulting particles were isolated by vacuum filtration and oven drying as described above.

Example 3

Isolation of Polymer Microparticles Comprising Various Co-Polymers

In a polypropylene cup, 0.08 g Tergitol-15-s-3 and 0.42 g Tergitol-15-s-40 as co-surfactant and surfactant were mixed for 15 seconds in a FlackTek SpeedMixer. 4.77 g MA-PDMS, 0.16 g TEB-PDA, 0.25 g methyl acrylate, and 0.30 g initial water were added with 15 s of mixing after each addition. To the contents were added an additional 20 ml of water in 2 ml increments with 15 s of mixing between increments to form an emulsion. The emulsion contents were then transferred to a glass jar containing 0.05 g acetic acid, 20.75 g deionized water and a stir bar. The sample was allowed to react and particles were recovered by vacuum filtration and oven dried overnight as described in Example 1.

The same procedure was followed using the substitute co-monomers and quantities indicated in Table 1.

TABLE 1

| Co-monomer (g) | Tergitol-15-s-3 (g) | Tergitol-15-s-40 (g) | TEB-PDA (g) | MA-PDMS (g) | Initial water (g) | Addn water (ml) | Acetic acid (g) | Water (g) |
|---|---|---|---|---|---|---|---|---|
| 0.25 benzyl methacrylate | 0.08 | 0.42 | 0.15 | 4.75 | 0.27 | 20 | 0.06 | 20.91 |
| 0.25 tetrahydrofuryl methacrylate | 0.08 | 0.42 | 0.14 | 4.79 | 0.30 | 20 | 0.05 | 19.99 |

Example 4

Isolation of Polymer Microparticles Comprising Hydroxyethyl Methacrylate Co-Polymer In a polypropylene cup, 0.08 g Tergitol-15-s-3 and 0.45 Tergitol-15-s-40 as cosurfactant and surfactant were mixed for 15 seconds in a FlackTek SpeedMixer. To the contents were added 0.15 g TEB-PDA, 0.26 g HEMA (2-hydroxyethyl methacrylate), and 4.76 g of MA-PDMS with 15 s mixing after each addition. Then, 0.26 g initial water was added and mixed for 15 s, and an additional 20 ml of water was added in 2 ml increments, mixing for 15 s between increments. Five milliliters of contents were then transferred to a glass jar containing 0.06 g acetic acid, 20.02 g deionized water and a stir bar and allowed to react with stirring. The particles were recovered by vacuum filtration and oven dried overnight as described in Example 1.

Example 5

Isolation of Polymer Microparticles Comprising Hydroxyethyl Methacrylate Co-Polymer In a polypropylene cup, 0.08 g Tergitol-15-s-3 and 0.45 Tergitol-15-s-40 as cosurfactant and surfactant were mixed for 15 seconds in a FlackTek SpeedMixer. To the contents were added 0.15 g TEB-PDA, 0.26 g HEMA (2-hydroxyethyl methacrylate), and 4.76 g of MA-PDMS with 15 s mixing after each addition. Then, 0.26 g initial water was added and mixed for 15 s, and an additional 20 ml of water was added in 2 ml increments, mixing for 15 s between increments. Five milliliters of contents were added to a glass jar containing 0.07 g acrylic acid and 18.91 g water and allowed to react with stirring at 200 rpm. The particles were recovered by vacuum filtration and oven dried overnight as described in Example 1.

Example 6

Isolation of Polymer Microparticles Comprising Hydroxyethyl Methacrylate Co-Polymer In a polypropylene cup, acetic acid was added to 2-hydroxyethyl methacrylate (HEMA) and MA-PDMS and mixed in a FlackTek SpeedMixer for 30 seconds. Surfactant Tergitol-15-s-40 and co-surfactant Tergitol-15-s-3 was added to the mixture along with initial water and mixed for an additional 30 seconds. Then the contents were diluted by adding 2 ml increments of water and mixing for 30 seconds after each increment for a total of 15 ml where the last increment is 3 ml. The emulsion was transferred to a clean beaker containing a stir bar and TEB-PDA initiator was added. The sample was allowed to react for 2 hrs, after which the particles were recovered by vacuum filtration and vacuum oven dried overnight as described in Example 1. The compositions of samples are listed in Table 2.

TABLE 2

| sample | MAPDMS (21784-14) | HEMA | % HEMA | acetic acid | Tergitol-15-S-40 | Tergitol-15-s-3 | initial water | TEBPDA |
|---|---|---|---|---|---|---|---|---|
| 5A | 4.76 | 0.25 | 5.03 | 0.09 | 0.20 | 0.08 | 0.31 | 0.14 |
| 5B | 4.26 | 0.75 | 15.02 | 0.09 | 0.18 | 0.08 | 0.33 | 0.13 |
| 5C | 3.80 | 1.26 | 24.84 | 0.10 | 0.18 | 0.08 | 0.32 | 0.13 |
| 5D | 3.50 | 1.50 | 30.02 | 0.10 | 0.21 | 0.08 | 0.33 | 0.13 |

All values are masses and units are in grams.

Example 7

Isolation of Polymer Microparticles Comprising Hydroxyethyl Methacrylate Co-Polymer In a polypropylene cup, acetic acid was added to 2-hydroxyethyl methacrylate (HEMA) and MA-PDMS and mixed in a FlackTek SpeedMixer for 30 seconds. Polyglycol-modified trimethylsilylated silicate surfactant (PG-MTSS) was added to the mixture along with initial water and mixed for an additional 30 seconds. Then the contents were diluted by adding 2 ml increments of water and mixing for 30 seconds after each increment for a total of 15 ml where the last increment was 3 ml. The emulsion was transferred to a clean beaker containing a stir bar and TEB-PDA initiator was added. The sample was allowed to react for 2 hrs, after which the particles were recovered by vacuum filtration and vacuum oven dried overnight as described in Example 1. The compositions of the samples are listed in Table 3.

TABLE 3

| Sample | MAPDMS (21784-14) | HEMA | % HEMA | Acetic acid | PGMTSS | initial water | TEB-PDA |
|---|---|---|---|---|---|---|---|
| 6A | 4.75 | 0.26 | 5.10 | 0.14 | 0.16 | 0.33 | 0.15 |
| 6B | 4.51 | 0.51 | 10.10 | 0.14 | 0.16 | 0.31 | 0.13 |
| 6C | 4.26 | 0.76 | 15.11 | 0.15 | 0.16 | 0.30 | 0.14 |
| 6D | 4.01 | 1.01 | 20.09 | 0.14 | 0.15 | 0.32 | 0.14 |
| 6E | 3.77 | 1.25 | 24.94 | 0.15 | 0.19 | 0.34 | 0.14 |
| 6F | 3.50 | 1.50 | 30.00 | 0.14 | 0.15 | 0.30 | 0.14 |

All values are masses and units are in grams.

Figure 1:
FIG. 1 is a dark field STEM image of the PDMS and HEMA copolymerized particles of Example 7, wherein the lighter density region (pHEMA) shows darker contrast.
Figure 2:
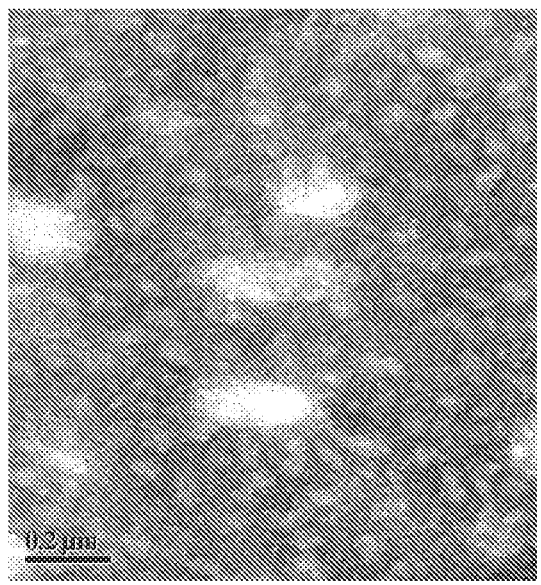
FIG. 2 is a bright field TEM image of the PDMS and HEMA copolymerized particles of Example 7, wherein the higher density region (PDMS) shows darker contrast.
Figure 3:
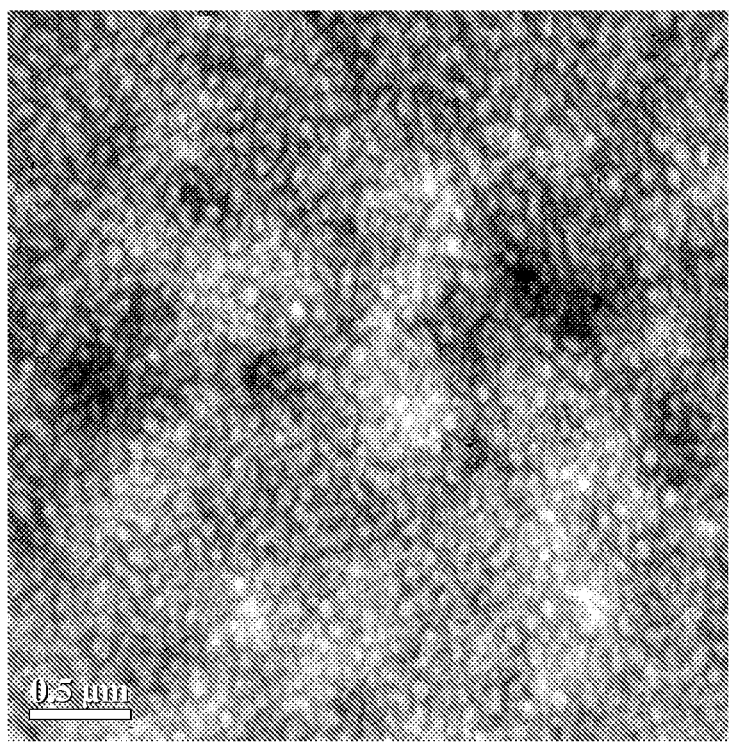
FIG. 3 is the TEM image of particles containing poly(dimethylsiloxane-co-isopropylacrylamide) prepared in a manner similar to Example 20, wherein the lighter regions are organic-rich hydrophilic phase and the darker regions are silicon-rich hydrophobic phase, and wherein the phase separation is on the order of 100 nm and not macrophase separated.
Figure 3:
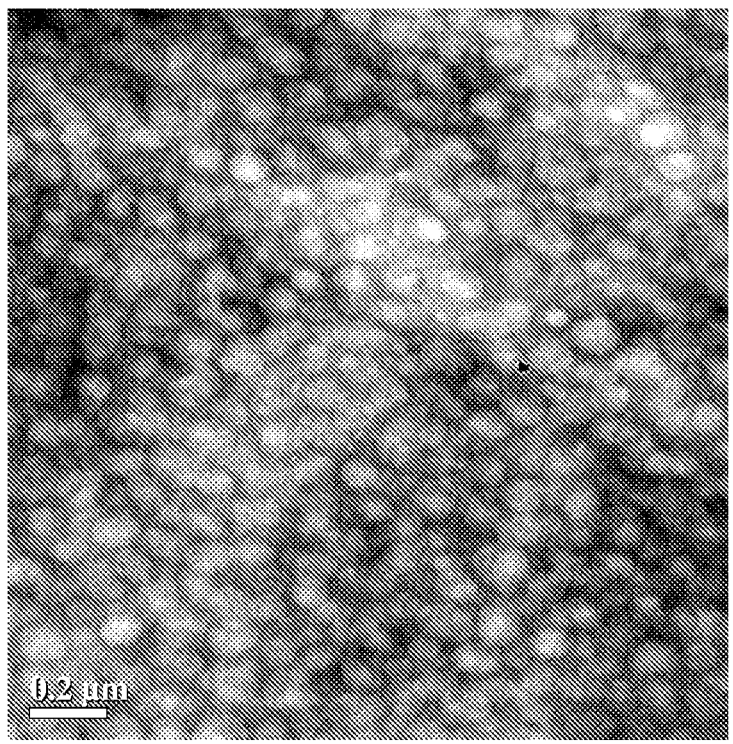

EELS analysis of PDMS and HEMA copolymerized particles (sample formulation shown in Table 4) incate that particles are nanophase segregated into pHEMA-rich domains that are interspersed within a PDMS matrix. Quantified phase maps (not shown) obtained by applying multiple least square fit to the core energy loss signals from the pure components and the particle specimen indicate that there was around 21% of HEMA in PDMS matrix in the EELS observed region. In a dark field STEM image of the inside structure of the particle (FIG. 1), lighter density region (pHEMA) reveals darker contrast, while heavier density region (PDMS) reveals darker contrast in the bright field TEM image (FIG. 2). The results indicate that the constituents of the particles do not undergo large scale phase separation into silicone-free bulk domains as by conventional free-radical based emulsion polymerization techniques, but rather form a particle that comprises microphase-separated organic rich domains in a continuous silicone matter. Also, agreement between the theoretical monomer loading and actual particle composition provides confirmation that the copolymerization efficiency is high.

TABLE 4

EELS Sample Formulation

| Contents | Mass (g) | by total weight |
|---|---|---|
| HEMA | 1.03 | 4.13 |
| MA-PDMS | 4.03 | 16.12 |
| TEB-PDA | 0.16 | 0.64 |
| Tergitol-15-s-40 | 0.45 | 1.78 |
| Tergitol-15-s-3 | 0.09 | 0.35 |
| initial water | 0.28 | 1.12 |
| additional water | 20.00 | 79.98 |
| Total | 25.00 | 100.00 |

Example 8

Isolation of Polymer Microparticles Using TEB-BI as the Free Radical Initiator

In a polypropylene cup, 0.46 g Tergitol-15-s-40 and 0.08 g Tergitol-15-s-3 were added as surfactant and co-surfactant and mixed for 15 s in FlackTek SpeedMixer. As an initiator, 0.16 g TEB-BI (triethylborane-butyl imidazole) was added which contains 4.6 wt % boron and mixed for 15 s. To the contents were added, 4.78 g MA-PDMS and 0.29 g 2-hydroxyethyl methacrylate with 15 s mixing after each addition. Then 0.28 g water was added and mixed for 15 s, and an additional 20 ml of water was added in 2 ml increments, mixing for 15 s after each increment. The sample was transferred to a clean glass jar and 0.06 g acetic acid was added to the sample for reaction. The particles were recovered by vacuum filtration and oven drying as described in Example 1.

Example 9

Isolation of Polymer Microparticles Using TEB-MOPA as the Free Radical Initiator In a polypropylene cup, 0.42 g Tergitol-15-s-40 and 0.08 g Tergitol-15-s-3 were mixed for 15 s in a FlackTek SpeedMixer. To the contents were added, 0.15 g TEB-MOPA (triethylborane-methoxypropylamine), 4.80 g MA-PDMS, 0.25 g HEMA, and 0.35 g water with 15 s mixing between additions. Additional water was added in 2 ml increments with 15 s mixing after each increment for a total of 20 ml. Five milliliters of the mixture was transferred to a clean vial and 0.06 g acetic acid was added and stirred at 200 rpm. The particles were recovered by vacuum filtration and oven drying as described in Example 1.

Example 10

Isolation of Polymer Microparticles Using Cetyltrimethyl Ammonium Chloride as Emulsifier In a polypropylene cup, 9.51 g MA-PDMS, 0.53 g 2-hydroxyethyl methacrylate, 0.23 g TEB-PDA were added and mixed for 15 s in a FlackTek SpeedMixer. To the contents was added 0.67 g of a 25 wt % aqueous solution of cetyltrimethyl ammonium chloride (Fluka purum CAS#112-02-7) and 0.31 g water with 15 s mixing after each addition. An additional 15 ml of water was added in ~2 ml increments and mixed for 15 s after each increment. Contents were transferred to a 4 oz squat glass jar and 0.08 g acetic acid and a stir bar were added and the stir plate was set to 250 rpm. The particles were recovered by vacuum filtration and oven drying as described in Example 1.

Example 11

Isolation of Polymer Microparticles Using Arquad 16-19 as Emulsifier

In a polypropylene cup, 4.79 g MA-PDMS and 0.26 g HEMA were added and mixed for 15 s in a FlackTek SpeedMixer. To the contents were added 0.11 g TEB-PDA and 0.34 g ethoxylated quaternary ammonium salt solution (Arquad-16-19, Akzo-Nobel) with 15 s mixing between each addition. Then 0.24 g water was added and mixed for 15 s. An additional 20 ml water was added in 2 ml increments and mixed after each increment for 15 s. The contents were transferred to a 4 oz glass jar and 0.04 g acetic acid and a stir bar were added and the sample was allowed to stir at 200 rpm. The particles were recovered by vacuum filtration and oven drying as described in Example 1.

Example 12

Isolation of Polymer Microparticles Using Ethyl Acetate Co-Solvent

In a polypropylene cup, 1.09 g Silmer® ACR-D2, multifunctional acrylate silicone pre-polymer (Siltech Corporation), and 0.52 g 2-hydroxyethyl methacrylate and 0.26 g ethyl acetate were added and mixed in a FlackTek SpeedMixer for 15 seconds. To the contents were added 0.03 g TEB-PDA, 0.19 g Tergitol-15-s-40, 0.07 g Tergitol-15-s-3, and 0.25 g water and mixed for 15 s. Additional water was added in the following increments: 0.25 g, 1.03 g, 2.69 g, 2.07 g, 2.18 g, and 2.23 g with mixing after each addition. Approximately 0.17 g acrylic acid was added and allowed to react while stiffing at 350 rpm. The procedure was repeated using Silmer® ACR Di-100, a 255 cP viscosity acrylate-terminated polydimethylsiloxane (Siltech Corporation) and different concentrations of the other components, as described in Table 5.

TABLE 5

| Silicone Polymer | HEMA | Ethyl acetate | Acid | Tergitol-15-s-40 | Tergitol-15-s-3 | Water | Addn water | TEB-PDA |
|---|---|---|---|---|---|---|---|---|
| 2.05 g ACR Di-100 | 1.02 g | 2.36 g | 0.11 g | 0.22 g | 0.14 g | 0.33 g | 10 ml | 0.08 g |
| 1.02 g ACR-D2 | 0.51 g | 0.12 g | 0.15 g | 0.18 g | 0.08 g | 0.26 g | 10 ml | 0.07 g |

Example 13

Use of Silicone Paste in an Antiperspirant 0.31 g C12-15 alcohols benzoate (Finsolv Tenn., Finetex, Inc.); 2.50 g Elastomer Paste (12% elastomer in D5 equivalent to 0.45 g of 5 wt % HEMA/PDMS particles and 3.29 g decamethylpentacyclosiloxane (D5) mixed together); 3.36 g of a mixture of dimethicone and trisiloxane fluid (30-60% Decamethyltetrasiloxane CAS Registry Number 141-62-8; 30-60% Octamethyltrisiloxane CAS Registry Number 107-51-7; 15-40% Dodecamethylpentasiloxane CAS Registry Number 141-63-9); 0.10 g of a powder of crosslinked dimethicone/vinyl dimethicone crosspolymer particles having a mean particle diameter of 5 μm; and 2.50 g of an antiperspirant active, aluminum-zirconium tetrachlilorohydrex-gly (REACH AZP 908 SUF) were mixed together using a FlackTek SpeedMixer for 15 seconds. The antiperspirant sample exhibited a granular texture and slightly lower viscosity than the control sample listed in subsequent example.

A control composition was prepared by mixing 0.30 g C12-15 alcohols benzoate (Finsolv Tenn., Finetex, Inc.); 3.74 g of a platinum cured silicone elastomer paste made following the procedure of Example 6 of U.S. Pat. No. 6,770,708 B2; 3.36 g of a mixture of dimethicone and trisiloxanefluid (30-60% Decamethyltetrasiloxane CAS Registry Number 141-62-8; 30-60% Octamethyltrisiloxane CAS Registry Number 107-51-7; 15-40% Dodecamethylpentasiloxane CAS Registry Number 141-63-9); 0.10 g of a powder of crosslinked dimethicone/vinyl dimethicone crosspolymer particles having a mean particle diameter of approximately 5 μm; and 2.55 g Antiperspirant Active, aluminum-zirconium tetrachlilorohydrex-gly (REACH AZP 908 SUF) together using a FlackTek SpeedMixer for 30 seconds. The resulting antiperspirant was textured and had medium viscosity.

Example 14

Properties of Polymeric Microparticles and Demonstration of Use of 1-Vinyl-2-Pyrrolidone as a Hydrophilic Co-Monomer A 3.00 g portion of MA-PDMS was added to a 40 ml polypropylene cup along with 2.00 g of 1-vinyl-2-pyrrolidone and 0.14 g of TEB-PDA initiator. The sample was mixed in a FlackTek SpeedMixer for 30 seconds. Then 0.07 g of Tergitol 15-S-3, 0.18 g of Tergitol 15-S-40, and 0.31 g of water were added. The sample was mixed for another 30 seconds. An additional 15 g of water was added in 2 g increments with 20 seconds of mixing between additions. To the emulsion was added 0.09 g of acetic acid dropwise, followed by 30 seconds of mixing on the dental mixer. A stir bar was added to the sample and allowed to mix on a stir plate for 2 hours. The particles were recovered using vacuum filtration through cellulose filter paper. The particles were dried overnight in a vacuum oven at ~35-50° C. Transmission optical microscopy (Zeiss Axioskop) and SEM (JEOL JSM-6335 FE-SEM) revealed spherical particles with diameters ranging from ~10-100 microns. ATR-IR (Thermo Nicolet 6700 equipped with a Smart MIRacle ATR accessory) confirmed the presence of the hydrophilic copolymer with an increase in the absorbance at ~1660 cm$^{-1}$.

Example 15

Properties of Polymeric Microparticles and Demonstration of Use of DMAEMA as a Hydrophilic Co-Monomer A 4.00 g portion of MA-PDMS was added to a 40 ml polypropylene cup along with 1.00 g of dimethylaminoethyl methacrylate (DMAEMA) and 0.13 g of TEB-PDA initiator. The sample was mixed in a FlackTek SpeedMixer for 30 seconds. Then 0.08 g of Tergitol 15-S-3, 0.20 g of Tergitol 15-S-40, and 0.31 g of water were added. The sample was mixed for another 30 seconds. An additional 15 g of water was added in 2 g increments with 20 seconds of mixing between additions. To the emulsion was added 0.09 g of acetic acid dropwise, followed by 30 seconds of mixing on the dental mixer. A stir bar was added to the sample and allowed to mix on a stir plate for 2 hours. The particles were recovered using vacuum filtration through cellulose filter paper and dried overnight in a vacuum oven at between 35-50° C. at a pressure of <25 mm Hg. Optical microscopy revealed spherical particles with diameters ranging from ~10-100 microns. ATR-IR confirmed the presence of the hydrophilic copolymer with an increase in the absorbance at ~1730 cm$^{-1}$.

Example 16

Properties of Polymeric Microparticles and Demonstration of Use of n-Vinyl Formamide as a Hydrophilic Co-Monomer A 3.50 g portion of MA-PDMS was added to a 40 ml polypropylene cup along with 1.50 g of n-vinyl formamide and 0.13 g of TEB-PDA initiator. The sample was mixed in a FlackTek SpeedMixer for 30 seconds. Then 0.10 g of Tergitol 15-S-3, 0.23 g of Tergitol 15-S-40, and 0.33 g of water were added. The sample was mixed for another 30 seconds. An additional 15 g of water was added in 2 g increments with 20 seconds of mixing between additions. To the emulsion was added 0.09 g of acetic acid dropwise, followed by 30 seconds of mixing on the dental mixer. A stir bar was added to the sample and allowed to mix on a stir plate for 2 hours. A portion of methanol was added to the sample to help break the emulsion and the solution was centrifuged. It separated into multiple layers and the particles were recovered and then vacuum filtered and rinsed with methanol. The particles were dried overnight in a vacuum oven as described in Example 16. Optical microscopy and SEM revealed spherical particles with diameters ranging from ~10-100 microns. ATR-IR confirmed the presence of the hydrophilic copolymer with an increase in the absorbance at ~1660 cm$^{-1}$.

Example 17

Isolation of Polymer Microparticles with Vinyl Pyridine Co-Polymer

A 4.50 g portion of MA-PDMS was added to a 40 ml polypropylene cup along with 0.50 g of 4-vinyl pyridine and 0.15 g of TEB-PDA initiator. The sample was mixed in a FlackTek SpeedMixer for 30 seconds. Then 0.08 g of Tergitol 15-S-3, 0.19 g of Tergitol 15-S-40, and 0.32 g of water were added. The sample was mixed for another 30 seconds. An additional 15 g of water was added in 2 g increments with 20 seconds of mixing between additions. To the emulsion was added 0.09 g of acetic acid dropwise, followed by 30 seconds of mixing on the dental mixer. A stir bar was added to the sample and allowed to mix on a stir plate for 2 hours. The particles were recovered using vacuum filtration through cellulose filter paper. The particles were dried overnight in a vacuum oven as described in Example 16.

Example 18

Properties of Polymeric Microparticles and Demonstration of Use of N,N,-dimethylacrylamide as a Hydrophilic Co-Monomer A 2.50 g portion of MA-PDMS was added to a 40 ml polypropylene cup along with 2.50 g of N,N,-dimethylacrylamide and 0.14 g of TEB-PDA initiator. The sample was mixed in a FlackTek SpeedMixer for 30 seconds. Then 0.07 g of Tergitol 15-S-3, 0.18 g of Tergitol 15-S-40, and 0.31 g of water were added. The sample was mixed for another 30 seconds. An additional 15 g of water was added in 2 g increments with 20 seconds of mixing between additions. To the emulsion was added 0.09 g of acetic acid dropwise, followed by 30 seconds of mixing on the dental mixer. A stir bar was added to the sample and allowed to mix on a stir plate for 2 hours. The particles were centrifuged with toluene. The solution separated into multiple layers and the particles were recovered and then vacuum filtered and rinsed with methanol. The particles were dried overnight in a vacuum oven as described in Example 16. Optical microscopy and SEM revealed spherical particles that were partially covered with irregularly shaped debris which is likely homopolymer. ATR-IR confirmed the presence of the hydrophilic copolymer with an increase in the absorbance at ~1630 $cm^{-1}$.

Example 19

Properties of Polymeric Microparticles and Demonstration of Use of N-isopropylacrylamide as a Hydrophilic Co-Monomer A 2.50 g portion of MA-PDMS was added to a 40 ml polypropylene cup along with 2.50 g of N-isopropylacrylamide and 0.13 g of TEB-PDA initiator. The sample was mixed in a FlackTek SpeedMixer for 30 seconds. Then 0.08 g of Tergitol 15-S-3, 0.21 g of Tergitol 15-S-40, and 0.27 g of water were added. The sample was mixed for another 30 seconds. An additional 15 g of water was added in 2 g increments with 20 seconds of mixing between additions. To the emulsion was added 0.09 g of acetic acid dropwise, followed by 30 seconds of mixing on the dental mixer. A stir bar was added to the sample and allowed to mix on a stir plate for 2 hours. The particles were recovered by vacuum filtration, rinsed with methanol, and dried overnight in a vacuum oven as described in Example 16. Optical microscopy and SEM revealed spherical particles with diameters ranging from ~10-100 microns. ATR-IR confirmed the presence of the hydrophilic copolymer with an increase in absorbance at ~1645 $cm^{-1}$.

Example 20

Demonstration of Use of Various Emulsifiers

A 2.51 g portion of MA-PDMS was added to a 40 ml polypropylene cup along with 2.50 g of N-isopropylacrylamide (IPAA) and 0.13 g of TEB-PDA initiator. The sample was mixed in a FlackTek SpeedMixer for 30 seconds. Then 0.24 g of PGMTSS and 0.31 g of water were added. The sample was mixed for another 30 seconds. An additional 15 g of water was added in ~2 g increments with 20 seconds of mixing between additions. To the emulsion was added 0.09 g of acetic acid dropwise, followed by 30 seconds of mixing on the dental mixer. A stir bar was added to the sample and allowed to mix on a stir plate for 2 hours. The particles were centrifuged with toluene. The solution separated into multiple layers and the particles were recovered and then vacuum filtered and rinsed with methanol. The particles were dried overnight in a vacuum oven as described in Example 16. Optical microscopy and SEM revealed spherical particles with diameters ranging from ~10-100 microns. ATR-IR confirmed the presence of the hydrophilic copolymer with an increase in absorbance at ~1645 $cm^{-1}$. Transmission electron microscopy (TEM) indicated that phase separation occurred on the order of 100 nm, confirming that the copolymer contained both a hydrophilic organic-rich phase and a silicon-rich hydrophobic phase that was not macro-phase separated.

Example 21

Demonstration of Use of Non-Acid Organonitrogen-Reactive Compounds

A 2.50 g portion of MA-PDMS was added to a 40 ml polypropylene cup along with 2.50 g of IPAA and 0.13 g of TEB-PDA initiator. The sample was mixed in a FlackTek SpeedMixer for 30 seconds. Then 0.24 g of PGMTSS and 0.26 g of water were added. The sample was mixed for another 30 seconds. An additional 15 g of water was added in ~2 g increments with 20 seconds of mixing between additions. To the emulsion was added 0.12 g of glycerol carbonate dropwise, followed by 30 seconds of mixing on the dental mixer. A stir bar was added to the sample and allowed to mix on a stir plate for 2 hours. The reaction seemed to proceed slower than with an acid decomplexer, but the particle size and yield were similar to when acetic acid was used. The particles were centrifuged with methanol. The solution separated into multiple layers and the particles were recovered and then vacuum filtered and rinsed with methanol. The particles were dried overnight in a vacuum oven as described in Example 16. Optical microscopy and SEM revealed spherical particles with diameters ranging from ~10-100 microns. ATR-IR confirmed the presence of the hydrophilic copolymer with an increase in absorbance at ~1645 $cm^{-1}$.

Example 22

Demonstration of Use of Non-Acid Organonitrogen-Reactive Compounds

A 2.50 g portion of MA-PDMS was added to a 40 ml polypropylene cup along with 2.50 g of N-isopropylacrylamide and 0.13 g of TEB-PDA initiator. The sample was mixed in a FlackTek SpeedMixer for 30 seconds. Then 0.26 g of PGMTSS and 0.27 g of water were added. The sample was mixed for another 30 seconds. An additional 15 g of water was added in ~2 g increments with 20 seconds of mixing between additions. To the emulsion was added 0.12 g of propylene carbonate dropwise, followed by 30 seconds of mixing on the dental mixer. A stir bar was added to the sample and allowed to mix on a stir plate for 2 hours. The reaction seemed to proceed slower than with an acid decomplexer, but the particle size and yield were similar to when acetic acid was used. The particles were centrifuged with water. The solution separated into multiple layers and the particles were recovered and then vacuum filtered and rinsed with methanol. The particles were dried overnight in a vacuum oven as described in Example 16. Optical microscopy and SEM revealed spherical particles with diameters ranging from ~10-100 microns. ATR-IR confirmed the presence of the hydrophilic copolymer with an increase in absorbance at ~1645 cm$^{-1}$.

Example 23

Demonstration of Compositional Range

Various samples were prepared in a manner identical to Example 20, but with varying ratios of MA-PDMS to IPAA such that the monomer composition ranged from 0 to 80 wt % IPAA. Specifically, the following samples were prepared: (i) 0 wt % IPAA; (ii) 19:1 ratio of MA-PDMS to IPAA such that the monomer composition was 5 wt % IPAA; (iii) 9:1 ratio of MA-PDMS to IPAA such that the monomer composition was 10 wt %; (iv) 4:1 ratio of MA-PDMS to IPAA such that the monomer composition was 20 wt % IPAA; (v) 2.3:1 ratio of MA-PDMS to IPAA such that the monomer composition was 30 wt % IPAA; (vi) 1.5:1 ratio of MA-PDMS to IPAA such that the monomer composition was 40 wt % IPAA; and (vii) 1:4 ratio of MA-PDMS to IPAA such that the monomer composition was 80 wt % IPAA.

Figure 4:
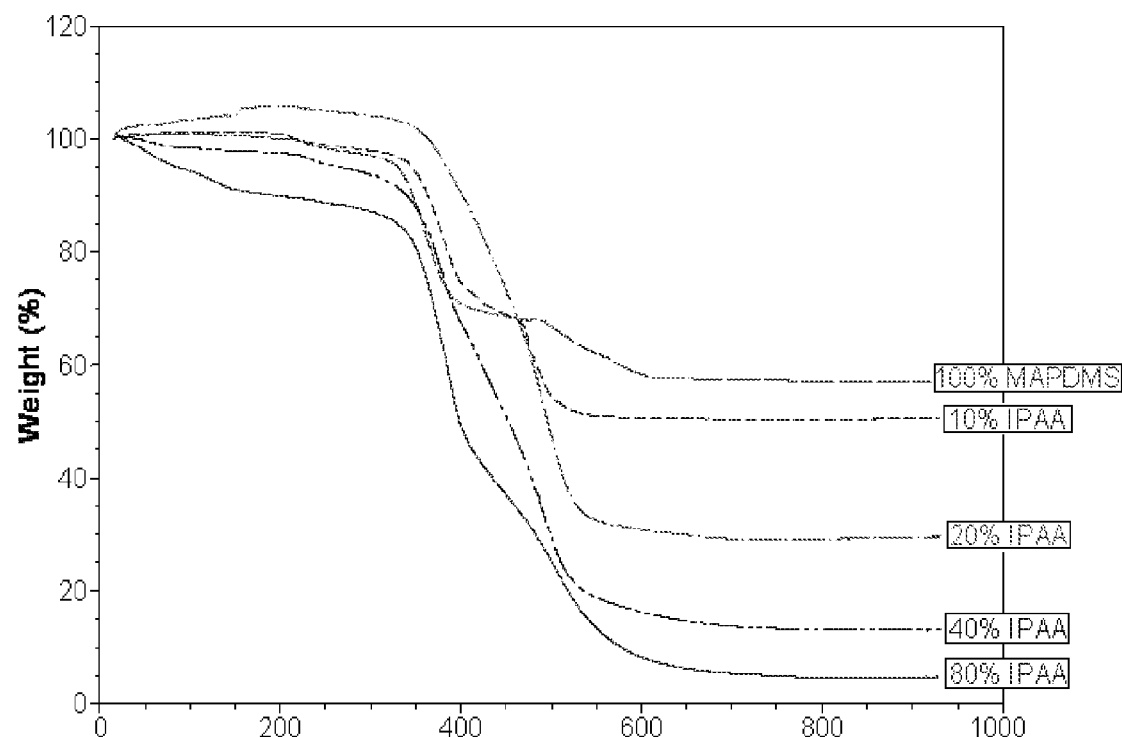
FIG. 4 shows the thermal gravimetric analysis of polymer particles containing poly(dimethylsiloxane-co-isopropylacrylamide) from Example 23, wherein the initial concentration of IPAA monomer varies from 0-80 wt %.

FIG. 4 shows the thermal gravimetric analysis profiles of polymer particles containing poly(dimethylsiloxane-co-isopropylacrylamide) wherein the initial concentration of IPAA was 0 wt %, 10 wt %, 20 wt %, 40 wt %, and 80 wt %. Samples were run in an air atmosphere. The particles containing only crosslinked silicone have the highest level of residue as stable silicate species are formed when the particles are heated. As the concentration of hydrophilic copolymer increases in the particles, the residue decreases as the hydrocarbon component degrades to volatile organic species when heated.

FIG. 5 shows the ATR-IR spectra of polymer particles containing poly(dimethylsiloxane-co-isopropylacrylamide) wherein the initial concentration of IPAA varies from 0 to 80 wt %. The amide I and II peaks, at 1640 cm$^{-1}$ and 1550 cm$^{-1}$ respectively, show a corresponding increase of the poly(N-isopropylacrylamide) in the polymer particles.

FIG. 6 shows the differential scanning calorimetry (DSC) of polymer particles containing poly(dimethylsiloxane-co-isopropylacrylamide) wherein the initial concentration of IPAA varies from 0 to 50 wt %. The siloxane component has a melting endotherm at −50° C. As the amount of IPAA monomer is increased in the formulation, the endotherm peak area decreases indicating poly(n-isopropylacrylamide) has taken the place of some of the siloxane. The presence of poly(n-isopropylacrylamide) in the particles is also indicated by the appearance of a glass transition temperature at ~140° C.

The present invention should not be considered limited to the specific examples described herein, but rather should be understood to cover all embodiments of the invention. Various modifications and equivalent processes, as well as numerous structures and devices, to which the present invention may be applicable will be readily apparent to those of skill in the art. Those skilled in the art will understand that various changes may be made without departing from the scope of the invention, which is not to be considered limited to what is described in the specification.

The invention claimed is:

1. A method for the preparation of a silicone composition, the method comprising:
    (I) co-polymerizing
        Component (A), at least one organopolysiloxane having an average of at least two free radical polymerizable groups per molecule that is selected from the group consisting of a methacryloxypropyl-terminated polydimethylsiloxane, an acryloxypropyl-terminated polydimethylsiloxane, an (acryloxypropyl) methylsiloxane-dimethylsiloxane copolymer; and a combination thereof; and
        Component (B), at least one organic co-monomer having an average of at least one free radical polymerizable group per molecule that is selected from the group consisting of benzyl methacrylate, tetrahydrofuryl methacrylate, 2-hydroxyethyl methacrylate, dimethylaminoethyl methacrylate, N-vinyl formamide, 4-vinyl pyridine, N,N-dimethylacrylamide, N-isopropylacrylamide, and a combination thereof, with a weight ratio of Component (A) to Component (B) of about 1:4 to about 19.2:1;
    wherein co-polymerization occurs in the presence of
        Component (C), at least one organoborane free radical initiator selected from the group consisting of triethylborane-propanediamine, triethylborane-butyl imidazole, triethylborane-methoxypropylamine, and a combination thereof;
        Component (D), water;
        Component (E), at least one organonitrogen-reactive compound; and
        oxygen;
    while maintaining a temperature of from about 5° C. to about 95° C. to form hydrophilically-modified silicone elastomeric microparticles; and
    (II) recovering the silicone elastomeric microparticles and dispersing them in at least one absorbable fluid that is immiscible with Component (D) to form a paste comprising the silicone elastomeric microparticles with at least some of the absorbable fluid absorbed therein.

2. The method according to claim 1, wherein the silicone elastomeric microparticles are formed by adding Component (C) to a dispersion or emulsion comprising Component (A), Component (B), Component (D), and Component (E) or by adding Component (E) to a dispersion or emulsion comprising Component (A), Component (B), Component (C) and Component (D).

3. The method according to claim 1, wherein the absorbable fluid is selected from silicones, including linear and cyclosiloxanes comprising decamethylcyclopentasiloxane and organic solvents, including C8-C20 isoparaffins, isododecane, isohexadecane, esters selected from isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-d isostearate, and any combination thereof.

4. The method according to claim 1, wherein the temperature is maintained at from about 10° C. to about 35° C.

5. The method according to claim 1, wherein optional Component (E) is selected from acetic acid, citric acid, acrylic acid, polyacrylic acid, isophorone diisocyanate, and any combination thereof.

6. The method according to claim 1, wherein co-polymerization occurs in the presence of, or the silicone elastomeric microparticles formed are treated with, Component (F), at least one active ingredient suitable for use in personal care and healthcare products.

7. The method according to claim 1, wherein co-polymerization occurs in the presence of Component (G), at least one emulsifier.

8. The method according to claim 6, wherein Component (F) is selected from vitamins, sunscreens, plant extracts, fragrances or perfumes, topical drug actives, proteins, enzymes, antiperspirants, deodorants, moisturizers, antifungal agents, antimicrobial agents, and any combination thereof.

9. The method according to claim 7, wherein Component (G) is selected from secondary alcohol ethoxylates, polyglycol-modified trimethsilylated silicate, polyglycol-modified siloxanes, polyglycol-modified silicas, ethoxylated quaternary ammonium salt solutions, cetyltrimethylammonium chloride solutions, and any combination thereof.

\* \* \* \* \*